US007771955B2

(12) United States Patent
Barbari et al.

(10) Patent No.: US 7,771,955 B2
(45) Date of Patent: Aug. 10, 2010

(54) AFFINITY MEMBRANE FOR CAPTURE OF A TARGET BIOMOLECULE AND FORMATION THEREOF BY SITE-DIRECTED IMMOBILIZATION OF A CAPTURE BIOMOLECULE

(75) Inventors: Timothy Alan Barbari, McLean, VA (US); Sufi Rizwan Ahmed, Hillsboro, OR (US)

(73) Assignee: University of Maryland, College Park, MD (US)

( * ) Notice: Subject to any disclaimer, the term of this patent is extended or adjusted under 35 U.S.C. 154(b) by 0 days.

(21) Appl. No.: 11/447,154

(22) Filed: Jun. 6, 2006

(65) Prior Publication Data

US 2006/0292680 A1  Dec. 28, 2006

Related U.S. Application Data

(60) Provisional application No. 60/688,852, filed on Jun. 9, 2005, provisional application No. 60/689,385, filed on Jun. 10, 2005.

(51) Int. Cl.
*G01N 33/53* (2006.01)
*C07F 15/04* (2006.01)
*C12P 21/02* (2006.01)

(52) U.S. Cl. .................. 435/7.1; 556/138; 435/69.1

(58) Field of Classification Search .................. 435/7.1, 435/69.1; 556/138

See application file for complete search history.

(56) References Cited

U.S. PATENT DOCUMENTS

2005/0260685 A1* 11/2005 Fang et al. ................... 435/7.1

OTHER PUBLICATIONS

Vijayendran et al., "A quantitative assessment of heterogeneity for surface-immobilized proteins," Anal Chem 73:471-480, 2001.*
Fenoll et al., "Oxidation by mushroom tyrosinase of monophenols generating slightly unstable o-quinones," Eur J Biochem 267:5865-5878, 2000.*
Waite, Evidence for a repeating 3,4-dihydroxyphenylalanine- and hydroxyproline-containing decapeptide in the adhesive protein of the mussel, *Mytilus edulis* L., J Biol Chem 258:5(2911-2915, 1983.*

* cited by examiner

*Primary Examiner*—Karen Cochrane Carlson
*Assistant Examiner*—Rosanne Kosson
(74) *Attorney, Agent, or Firm*—Jonathan E. Grant; Grant Patent Services

(57) ABSTRACT

Compositions and methods are taught for directing the orientation of an immobilized capture biomolecule on a hydrophobic membrane. The method comprises layering at least one tie layer on a hydrophobic membrane, adding an amine functional layer on top of at least one tie layer; and attaching an alignment biomolecule to the amine functional layer. The alignment biomolecule has the ability to either capture a target biomolecule itself and thus be considered a capture biomolecule, or bind and orient the immobilized capture biomolecule so as to maximize the binding activity of the immobilized capture biomolecule. In one embodiment, a nickel-coordinated amine functional layer binds with a histidine-tagged alignment biomolecule. In another embodiment, an amine functional layer reacts, via tyrosinase catalysis, with a tyrosine residue in an alignment biomolecule.

3 Claims, 24 Drawing Sheets

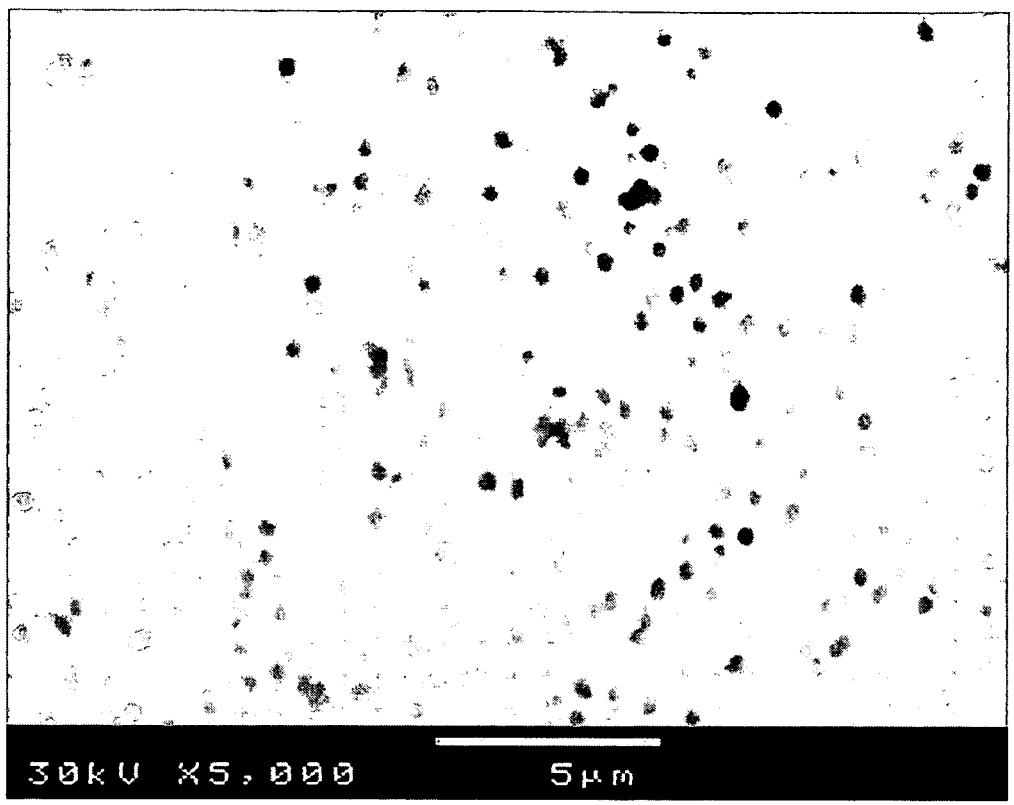
(a)
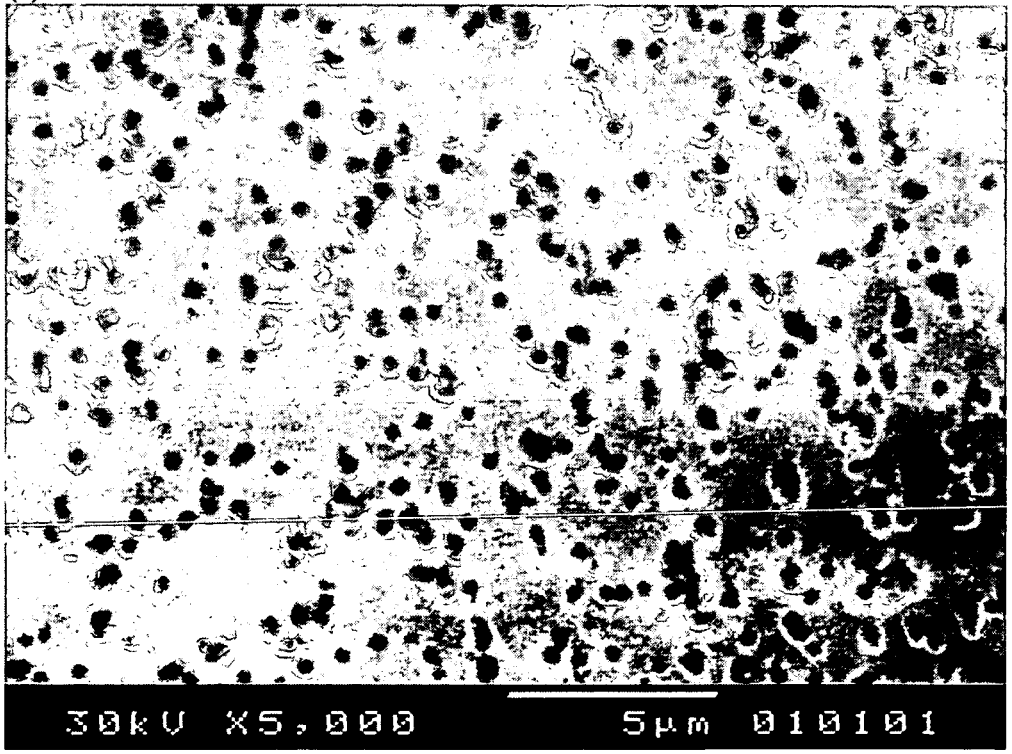
(b)
Figure 4

(a)
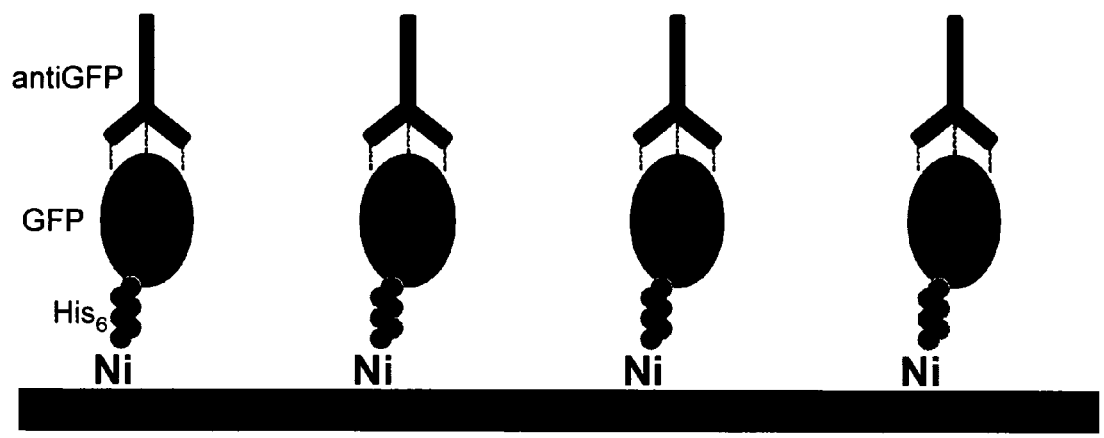
(b)
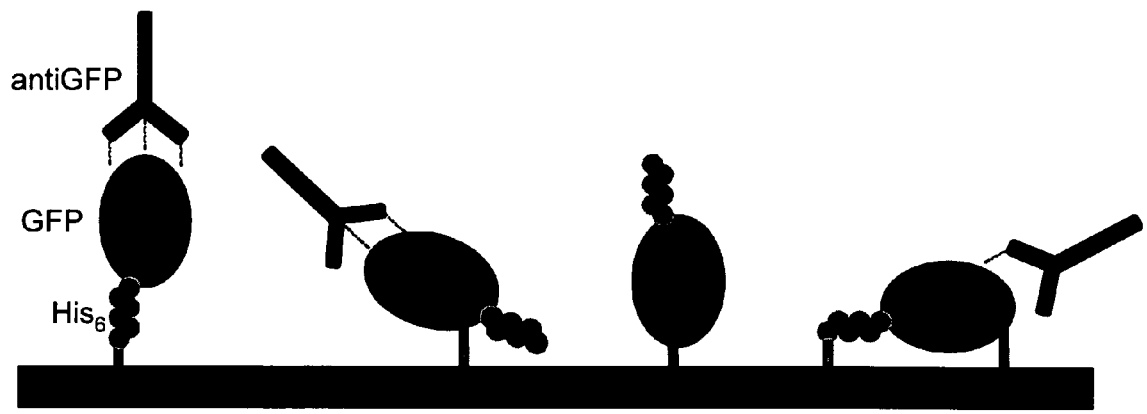
Figure 9

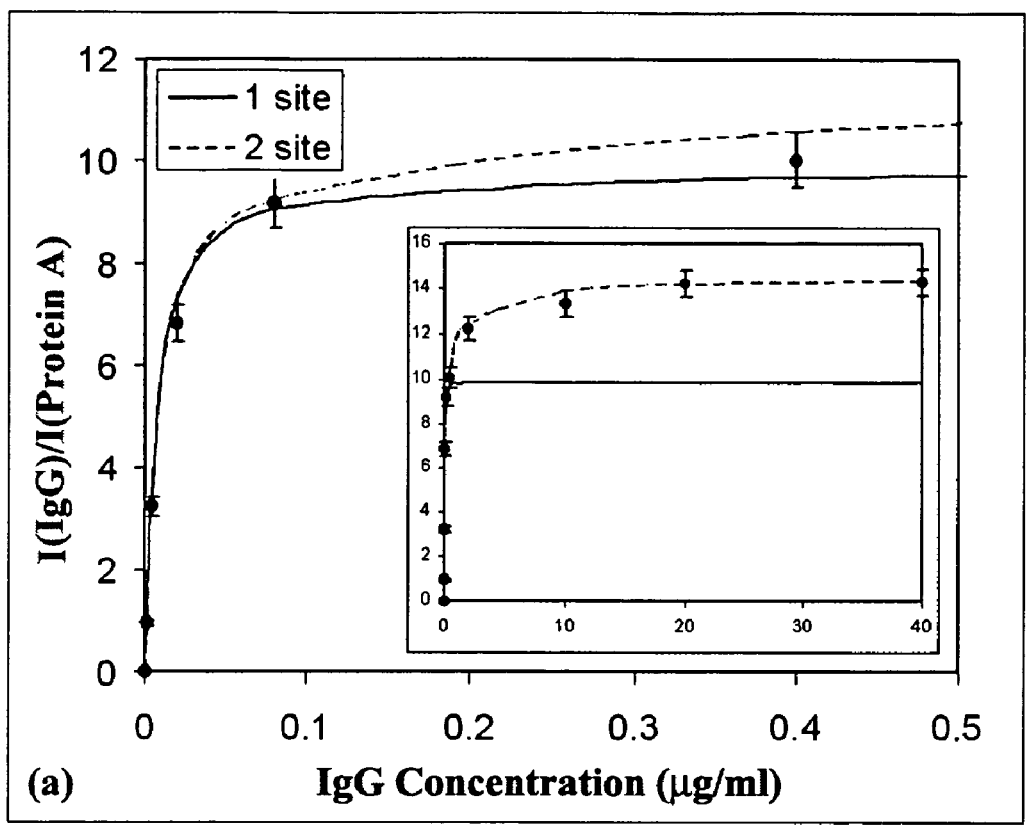
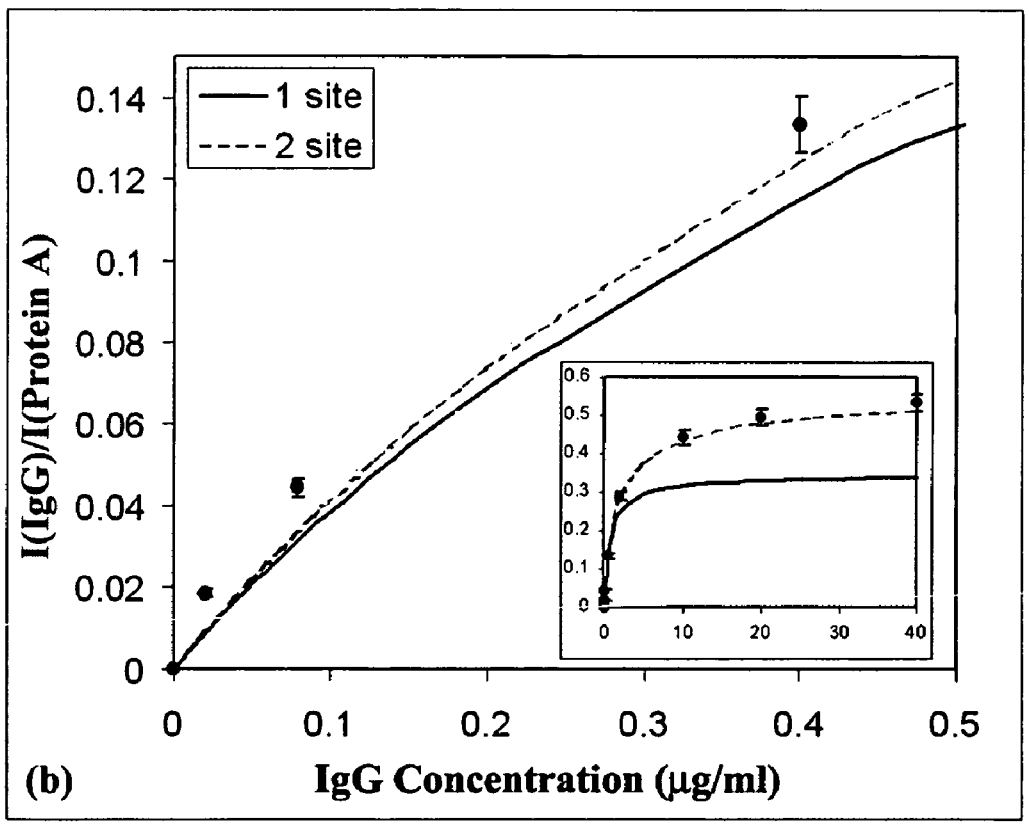
Figure 17

(a)
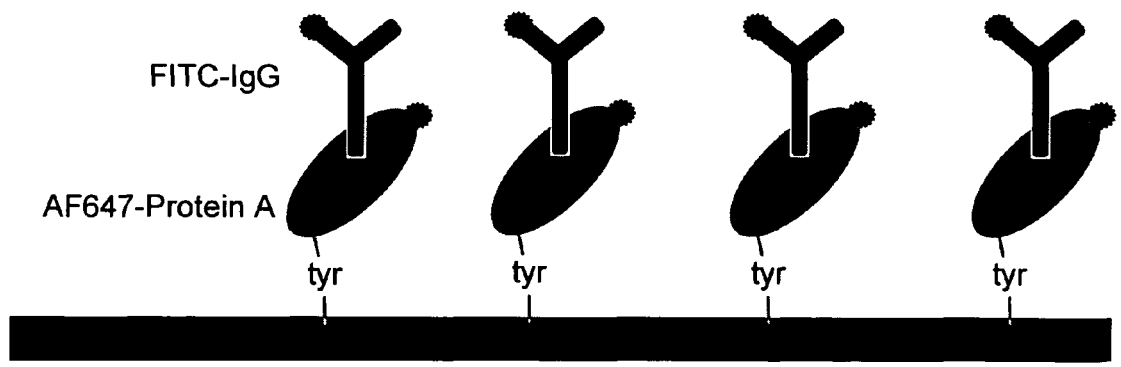
(b)
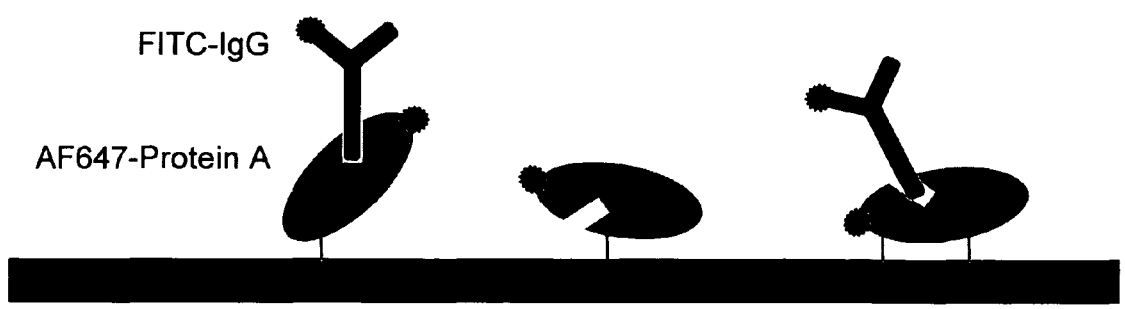
Figure 18

AFFINITY MEMBRANE FOR CAPTURE OF A TARGET BIOMOLECULE AND FORMATION THEREOF BY SITE-DIRECTED IMMOBILIZATION OF A CAPTURE BIOMOLECULE

This application claims priority to U.S. Provisional Application 60/688,852, filed Jun. 9, 2005, and U.S. Provisional Application 60/689,385, filed Jun. 10, 2005, incorporated herein by reference.

FIELD OF THE DISCLOSURE

The present disclosure is directed to affinity membranes for the capture of target biomolecules, distinguished by surfaces with capture biomolecules immobilized in a preferred orientation.

BACKGROUND OF THE DISCLOSURE

Layered expression scanning (LES), or multimembrane blotting, is a recently developed method for the high-throughput analysis of proteomic profiles from multiple samples of physiological fluids or tissue sections (See C. R. Englert, et al, "Layered expression scanning; Rapid molecular profiling of tumor samples," Cancer Res., 60 (2000) 1526; A. L. Feldman et al., "Modulation of tumor-host interactions, angiogenesis, and tumor growth by tissue inhibitor of metalloproteinase 2 via a novel mechanism," Cancer Res., 64 (2004) 4481, incorporated herein by reference). If applied to a 2-D gel, in which proteins have been separated by molecular weight in one dimension and by charge in the other, LES provides a third dimension related to protein function.

As originally developed, a layered stack of membranes with straight-through pores is used, onto which proteins bind nonspecifically to each membrane during sample transfer. After transfer through the stack, each membrane is exposed to a different antibody that binds to a particular protein of interest. Low porosity membranes with straight-through pores are used, rather than the highly-porous nitrocellulose or PVDF membranes with interconnected pores traditionally used in blotting, to prevent image distortion due to lateral diffusion, thus producing "carbon copies" of each sample from a single transfer. Minimal lateral diffusion is particularly important for maintaining morphological features in tissue sections.

However, as a result of nonspecific binding (universal capture), proteins are depleted as they pass through the membrane stack. This can significantly reduce the sensitivity of the multimembrane approach and, as a result, only a limited number of proteins can be analyzed. Therefore, there is significant motivation to develop affinity or "smart" membranes, each of which can selectively capture one specific protein. A highly selective affinity membrane will drastically reduce protein depletion and increase the sensitivity of the LES technique. Such a membrane will also be advantageous in conventional blotting if the target protein is present at very low concentrations.

The development of an affinity membrane for blotting applications requires the immobilization of capture biomolecules (antibodies, proteins, polypeptides) on the surface of a base membrane. The immobilization of an antibody (IgG) to a solid surface is currently used in a number of diagnostic assays, such as the enzyme-linked immunosorbent assay (ELISA) and antibody arrays. The primary challenges for creating any surface with immobilized proteins are to prevent denaturing during immobilization and to orient the proteins to maintain bioactivity.

A method and composition for the identification of a target biomolecule in a sample has been developed. The method comprises obtaining a stack of coated capture membranes comprising a plurality of capture membranes, each coated with a different capture biomolecule. The membrane stack is exposed to a sample, and, after a given amount of time for the sample to permeate the membrane stack, the membrane stack is removed from the sample carrier and the capture membrane to which the target biomolecule adheres is identified. However, there are differences between antibodies and other proteins or peptides that require different techniques for attachment to a membrane.

For antibodies, attachment entails immobilizing the Fc tail such that the Fab fragments, where specific target binding occurs, are accessible and properly oriented. Several different methods have been reported in the literature for surface immobilization of antibodies. These techniques include: (1) direct spotting of antibody on a solid surface (Knezevic, V, Proteomic profiling of the cancer microenvironment by antibody arrays," Proteomics, 1 (2001) 1271, incorporated herein by reference); covalent attachment of antibody on a chemically activated surface using glutaraldehyde chemistry or through a variety of other chemistries, (Angenendt, et al., "Toward optimized antibody microarrays: a comparison of current microarray support materials,"Anal. Biochem., 309 (2002) 253; W. Kusnezow, et al, "Antibody microarrays: An evaluation of production parameters, " Proteomics, 3 (2003) 254; and U. B. Nielsen et al."Multiplexed sandwich assays in microarray format," J. Immunol. Methods, 290 (2004) 107 (herein incorporated by reference); an (3) immobilization via affinity tags (H. Zhu et al., "Global analysis of protein activities using proteome chips," Science, 293 (2991) 2101 and Johnson, C. P. et al, "Engineered protein A for the orientational control of immobilized proteins," Bioconjugate Chem., 14 (2003) 974 incorporated herein by reference); (4) biotinylation of capture molecules and their immobilization on streptavidin coated support (Delehanty, J. B. et al, "A microarray immunoassay for simultaneous detection of proteins and bacteria," Anal. Chem., 74 (2002) 5681 and Peluso, P. et al. "Optimizing antibody immobilization strategies for the construction of protein microarrays,"Anal. Biochem., 312 (2003) 113, herein incorporated by reference); (5) immobilization of IgG on Protein A or Protein G coated surfaces (Kumar, A. et al. "Emerging technologies in yeast genomics," Nat. Rev. Genet., 2 (2001) 302 and Vijayendran, R. A. and Leckband, D. E., "A quantitative assessment of heterogeneity for surface-immobilized proteins,"Anal. Chem., 73 (2001) 471, incorporated herein by reference); (6) DNA-directed immobilization (DDI) for proper orientation of antibodies (Wacker, R. et al. Performance of antibody microarrays fabricated by either DNA-directed immobilization, direct spotting, or streptavidin-biotin attachment: a comparative study," Anal. Biochem., 330 (2004) 281, herein incorporated by reference); and (7) cutinase- or AGT-fusions (Kwon, Y. et al. "Antibody arrays prepared by cutinase-mediated immobilization on self-assembled monolayers," Anal. Chem., 76 (2004) 5713 and Sielaff, I. et al. "Protein function microarrays based on self-immobilizing and self-labeling fusion proteins," Chem Bio Chem, 7 (2006) 194, herein incorporated by reference).

One of the most commonly used methods to immobilize proteins is the nonspecific reaction of amine groups, both on the surface and in the protein, with glutaraldehyde Given the large number of amino acid residues with pendant amine groups in a typical protein, this approach often crosslinks the protein, leading to significant denaturing and a small fraction of active protein. For example, amine functional surfaces have been reacted with Protein A or Protein G to take advantage of the ability of these proteins to bind to the Fc tail on IgG as a means of orienting antibodies on the surface. Although the use of Protein A (or G) improves the activity of antibody relative to glutaraldehyde immobilization of the antibody itself, a significant fraction of the Protein A (or G) is denatured during surface immobilization and cannot orient antibodies properly upon binding.

One method for improving the number of active biomolecules on a surface is to use specific biological interactions to link the biomolecule to the surface in an effort to control its orientation. An example for the use of such interactions is immobilized metal affinity chromatography (IMAC), which is based on the chelation of specific amino acids, such as histidine, to cations, such as $Ni^{++}$, that are bound to groups in the polymeric media. Histidine tags are often engineered onto the terminal ends of proteins specifically for separation on IMAC columns. Recently, it was reported that the immobilization of hexahistidine-tagged Protein A (his-Protein A) on $Ni^{++}$-nitrilotriacetic acid (NTA) and $Ni^{++}$-hydrosuccinimide derivative surfaces demonstrated that his-Protein A can properly orient IgG. (See Johnson, infra).

SUMMARY OF THE DISCLOSURE

In this disclosure, alignment biomolecules (proteins or peptides) are immobilized on a membrane surface in preferred orientations. The alignment biomolecule can serve as the capture biomolecule itself, or if said alignment biomolecule is an Fc-binding biomolecule, an antibody can be bound to the alignment biomolecule, which, in turn, can serve as the capture biomolecule. The present methods and compositions prevent or greatly limit denaturation of the immobilized capture biomolecules, thereby allowing for an increase in the number of target binding sites, thus allowing for the favorable orientation of said capture biomolecules.

One embodiment of the disclosure comprises layering at least one tie layer on a hydrophobic membrane and adding an amine-functional layer on top of the tie layer. This is followed by the immobilization of an alignment biomolecule to the amine functional layer, wherein the alignment biomolecule has the ability to orient an antibody so as to maximize the binding activity of said immobilized biomolecule.

The hydrophobic membrane may be a thin porous substrate. In one embodiment of the disclosure, the membrane consists of straight-through pores that are not interconnected. In another embodiment of the disclosure, the membrane is track-etched. In another embodiment of the disclosure, the membrane is comprised of polycarbonate. A plurality of said membranes may be stacked. Each membrane of the stack contains a different capture biomolecule, such that the membrane stack has the ability to test for a number of different target biomolecules.

The tie layer positioned on top of the membrane should have a surface tension between the surface tension of the membrane and the surface tension of the amine functional layer. In one embodiment of the disclosure, the tie layer is poly(vinyl acetate). In another disclosure, the tie layer is poly(vinyl butyral). In other embodiments of the disclosure, other tie layers may be used. The tie layer can be any polymer that (1) is soluble (<1% w/v) in either pure ethanol or an ethanol/acetone mixture of at least 50% ethanol by volume, and (2) contains pendant acetal or ester groups based on short-chain aldehydes or carboxylic acids, respectively. Examples include poly(vinyl acetate), poly(vinyl propionate), poly(vinyl n-butyrate), poly(vinyl iso-butyrate), poly(vinyl propional), and poly(vinyl butyral). Also, copolymers of these with poly(vinyl alcohol) can also serve as tie layers.

1. Site-Directed Immobilization Through Histidine

One embodiment of the disclosure uses an amine-functional layer consisting of nickel-coordinated chitosan. A chitosan layer may be first layered over said tie layer, followed by the nickel-coordinated chitosan being layered over the chitosan layer.

The alignment biomolecule may then be immobilized to the chitosan nickel layer.

In one embodiment of the disclosure, the alignment biomolecule is a histidine-tagged, Fc-binding protein or peptide.

In another embodiment of the disclosure, the alignment biomolecule is histidine-tagged Protein A.

In another embodiment of the disclosure, the alignment biomolecule is histidine-tagged Protein G.

In yet another embodiment of the disclosure, the alignment biomolecule is histidine-tagged hybrid Protein A/G.

In other embodiments of the disclosure, other histidine-tagged alignment peptides can be used.

In a further embodiment of the disclosure, the histidine tag consists of one to six terminal histidine residues.

In another embodiment, histidine-tagged, Fc-binding biomolecules are chelated to $Ni^{++}$ ions that are coordinated to functional groups on the membrane surface, thereby allowing for the favorable orientation of antibodies.

In yet another embodiment, antibodies are bound, through their Fc tails, to the immobilized histidine-tagged Fc-binding biomolecules. The Fab fragments of the antibodies, now oriented, are more accessible to protein antigen targets, thereby increasing the sensitivity of a membrane-based assay. Said antibodies, bound to the histidine-tagged, Fc-binding biomolecules, are capture biomolecules. Capture biomolecules can be used to capture target biomolecules in physiological samples, such as blood.

In yet another embodiment of the disclosure, other amine-functional layers can be substituted for chitosan. Any polymer with pendant primary amines can be used.

In one embodiment of the disclosure, the alignment biomolecule is any histidine-tagged biomolecule.

In another embodiment, the histidine-tagged biomolecule is a capture biomolecule, capable of capturing target biomolecules. Examples include a protein antigen as capture biomolecule and an antibody as target biomolecule.

2. Site-Directed Immobilization Through Tyrosine

One embodiment of the disclosure uses an amine-functional layer consisting of polyallylamine.

In one embodiment of the disclosure, a tyrosine residue in the alignment biomolecule is converted to o-quinone, which is then attached to the polyallylamine.

In one embodiment of the disclosure, o-quinone is produced by exposing the alignment biomolecule to tyrosinase, thereby converting said tyrosine in the alignment biomolecule to o-quinone.

In another embodiment of the disclosure, said o-quinone reacts with an amine group in polyallylamine to align biomolecule.

In one embodiment of the disclosure, the alignment biomolecule is an Fc-binding protein or peptide.

In another embodiment of the disclosure, the alignment biomolecule is Protein A.

In another embodiment of the disclosure, the alignment biomolecule is Protein G.

In yet another embodiment of the disclosure, the alignment biomolecule is hybrid Protein A/G.

In other embodiments of the disclosure, other tyrosine-containing alignment peptides can be used.

In yet another embodiment, antibodies are bound, through their Fc tails, to the Fc-binding biomolecules, immobilized through tyrosine residues. The Fab fragments of the antibodies, now oriented, are more accessible to protein antigen targets, thereby increasing the sensitivity of a membrane-based assay. Said antibodies, bound to the immobilized Fc-binding biomolecules, are capture biomolecules. Capture biomolecules can be used to capture target biomolecules in physiological samples, such as blood.

In yet another embodiment of the disclosure, other amine-functional layers can be substituted for polyallylamine. Any polymer with pendant primary amines can be used.

In one embodiment of the disclosure, the immobilized alignment biomolecule is any tyrosine containing biomolecule.

In another embodiment, the immobilized, tyrosine-containing biomolecule is a capture biomolecule, capable of capturing target biomolecules. Examples include a protein antigen as capture biomolecule and an antibody as target biomolecule.

In another embodiment of the disclosure, the antibody being aligned is an anti-antibody.

The disclosure may be described in terms of the x-y plane (dimension) of the biological sample platform (e.g., a multi-well plate), and the z-dimension representing the stack of layered capture membranes. Such an arrangement allows for the testing or profiling of numerous samples at one time. A single test can easily be performed for 50-100 or more antibodies, which will produce thousands of measurements in minutes.

There are advantages to detecting a target biomolecule (antigen, antibody or analyte) with an antibody coated membrane. Antibodies are highly specific and under the proposed disclosure will be extremely sensitive given the fact that all, or virtually all, of the antibody Fab fragments will be oriented so as to have maximum exposure to any target in a sample. Hence, cancer antigens can be more easily detected. By coating an entire surface with the specific capture antibody (antibodies), the specific antibody being tested will more readily bind the intended target. Accuracy is thus assured.

In one embodiment of the disclosure, a Layered Antibody Array (LAA) can serve as a screening tool by detecting antigens, analytes, or other antibodies in a highly multiplexed format. Approximately 5,000 measurements per experiment are capable of being performed at one time.

In yet another embodiment of the disclosure, the system and method may be used to screen for numerous diseases at one time.

This disclosure also allows for patient sera to be tested for the presence of any one of a relatively large panel of antigens or antibodies against unique antibodies expressed by neoplastic cells.

In yet another embodiment of the disclosure, sera samples can be screened for a panel of antigens or antibodies directed against toxic or infectious agents, or similarly, samples can be directed against antigens that are expressed as a result of toxic or infectious agents.

Before proceeding further, a definition of the terms used and their applicability to the disclosure is needed.

"Affinity" means specific attraction or force between biomolecules.

"Alignment" means the site-directed attachment of a biomolecule to optimize affinity between it and a target biomolecule.

"Antibody" refers to polyclonal, monoclonal, or chimeric antibodies and includes any portion of an antibody or a fragment of an antibody, such as a Fab fragment, as long as it is capable of binding to an antigen. The antibody, or portion thereof, may be purified, recombinant, or synthetic.

"Antigen" means any material that elicits production of, or is specifically bound by, one or more antibodies.

"Biomolecules" are molecules typically produced by living organisms. These molecules may include peptides, proteins, glycoproteins, nucleic acids, fatty acids, and carbohydrates and antibodies. Here, they specifically refer to peptides, polypeptides, proteins, antibodies, or any long chain molecule consisting of a sequence of amino acids.

"Capacity" means the ability to receive, hold, or absorb biomolecules from the sample.

"Capture Biomolecule" is a peptide or protein that is anchored to a membrane and has an affinity (such as a selective affinity) for one of the target biomolecules in the sample.

"Membrane" means a thin sheet of natural or synthetic material that is porous or otherwise at least partially permeable to biomolecules.

"Peptides" are a composed of acid units (amino acids) chemically bound together with amide linkages (CONH) with elimination of water. Peptides can be as few as two or three units in length, or up to twenty or more units. For the purpose of this disclosure, any reference to "peptide" may include one or more peptide strands, except where otherwise indicated.

"Proteins" are polypeptides normally having a specific biological function.

"Sample" means a material that contains biomolecules. A sample in this case may typically include tissue, gels, bodily fluids, and individual cells in suspensions or in pellet form, as well as materials in containers of biomolecules such as microtiter plates.

"Stack" refers to adjacent membranes, whether stacked horizontally, vertically, at an angle, or in some other direction. The membranes may be spaced or touching, and may be contiguous.

"Target Biomolecule" is a biomolecule that one seeks to identify, analyze, or measure in a sample that has an affinity for the capture biomolecule.

"Tie Layer" refers to any polymeric material added between the porous support and the amine-functional layer to promote the adherence of the amine-functional layer to the porous support.

With the foregoing and other objects, advantages and features of the disclosure that will become hereinafter apparent, the nature of the disclosure may be more clearly understood by reference to the following detailed description of the disclosure, the appended claims and to the several views illustrated in the drawings.

BRIEF DESCRIPTION OF THE FIGURES

FIG. 4 is a monograph of ESEM images of (a) PC and (b) PC-chitosan-$Ni^{++}$ membrane;

FIG. 9 is a schematic illustration of antiGFP binding to an affinity membrane based on (a) oriented his-GFP immobilized via Ni$^{++}$ chelation and (b) random his-GFP immobilized via glutaraldehyde reaction;

FIG. 17 are graphs showing the effect of IgG concentration on IgG binding to (a) PC-PAA-(tyr)Protein A, and (b) PC-PAA-(g)Protein A membranes. The solid line is the single-site Langmuir fit, and the dotted line is the two-site Langmuir fit;

FIG. 18 is a schematic illustration of antibody attached to an affinity membrane based on (a) favorably oriented Protein A immobilized via tyrosinase-catalyzed reaction and (b) randomly oriented Protein A immobilized via glutaraldehyde reaction. The asterisks represent fluorescent tags. Weak binding due to unfavorable orientation suggested on far right in (b);

DETAILED DESCRIPTION OF THE DISCLOSURE

Figure 24:
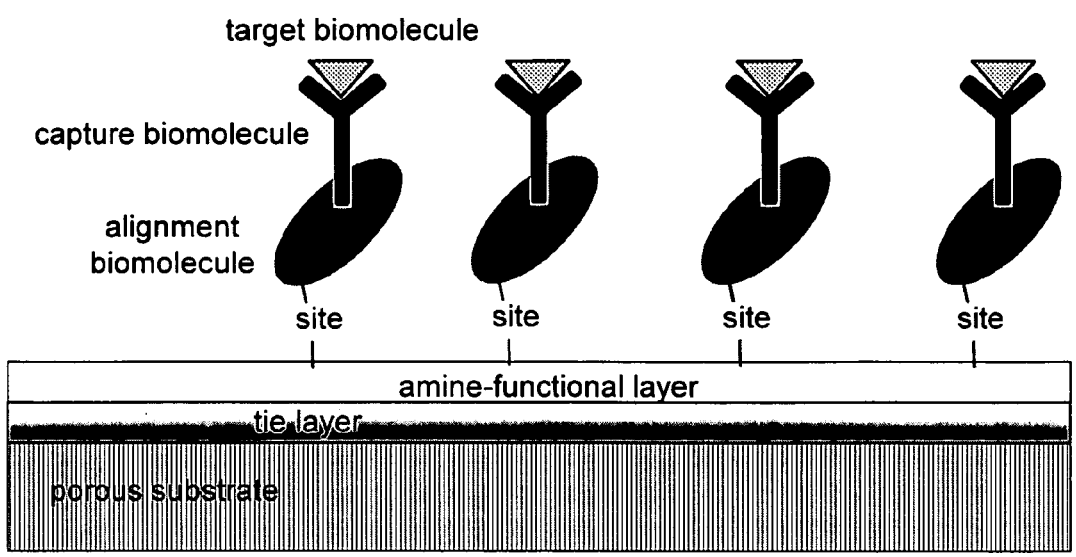
FIG. 24 is a schematic illustration of an affinity membrane for the capture of a target biomolecule by site-directed immobilization of a capture biomolecule.

The site-directed orientation of capture biomolecules, particularly antibodies, on a membrane surface, requires a functional surface to which said biomolecules (or alignment biomolecules) can be attached using specific chemical interactions, such as chelation, coordination, or covalent reaction (FIG. 24).

Figure 10:
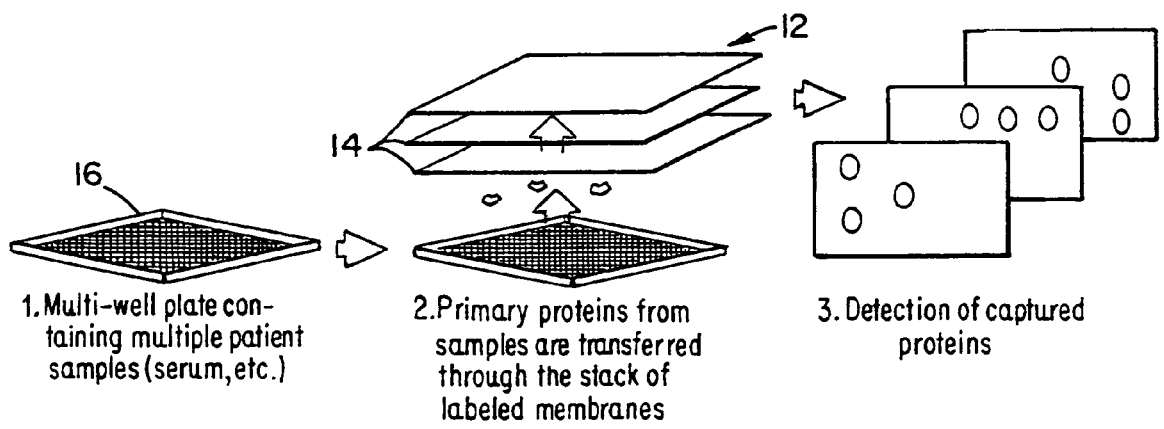
FIG. 10 is a schematic illustration of direct protein capture by the LAA system.
Figure 11:
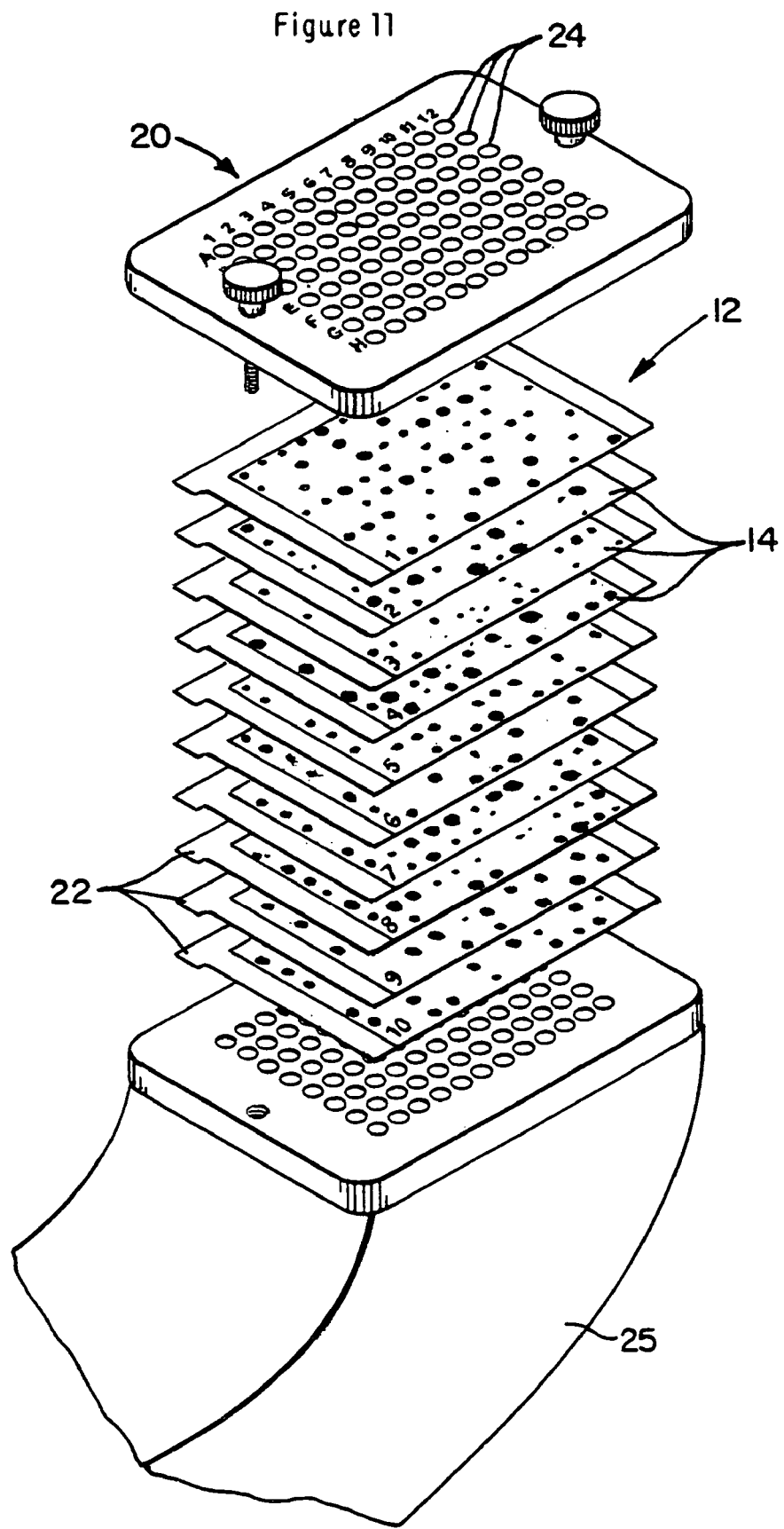
FIG. 11 is an exploded view of the membrane stack, wells and vacuum system; principal component analysis (PCS) clustering for patients and controls.

Referring to FIGS. 10 and 11, the number of membranes 14 in stack 12 may be as few as two or as many as 100. The number of membranes in a stack depends largely on the number of targets sought to be identified in the sample. Each membrane is preferably coated with a different capture biomolecule specific to a particular target of interest.

The membranes 14 are preferably constructed of a thin, low-porosity porous substrates with straight-through pores that are coated with capture biomolecules. The substrate is preferably constructed of polycarbonate or a similar polymeric material that maintains sufficient structural integrity despite being made porous and very thin. In lieu of polycarbonates, this material may include, for example, polyester or polyethylene terephthalate. The membrane may also be comprised of a cellulose derivative such as cellulose acetate, polyolefins, (e.g., polyethylene, polypropylene, etc.), or other porous materials., including ceramics or metals.

In one aspect of the disclosure, the substrates may be "track-etched membranes" (a/k/a "screen membranes"). These membranes are formed by a process that creates well-defined pores by exposing a dense film to ionizing radiation forming damage tracks. This is followed by etching of the damaged tracks into pores by a strong alkaline solution. A description of this process may be found on the Internet site of General Electric Water Technologies (Trevose, Pa.) at http://www.gewater.com/library/tp/322_Basic_Principles.jsp under the heading, "Basic Principles of Microfiltration" (herein incorporated by reference). Examples of membranes that may be employed as the substrate include the Isopore™ (polycarbonate film) membrane available from Millipore (Billerica, Mass.), the Poretics® Polycarbonate or Polyester membranes available from GE Osmonics Labstore (Trevose, Pa.), or the Cyclopore™ Polycarbonate or Polyester membranes available from Whatman (Clifton, N.J.).

In lieu of a track-etched membrane, a depth or tortuous pore membrane might be employed if its capacity can be rendered low enough to permit a stack of three of more such membranes to be used in the present disclosure. This could be accomplished, for, by example, casting the membrane very thin, far thinner than the thickness of depth membranes conventionally employed (150 microns). Alternatively, blocking certain binding sites could lower the capacity of conventional depth membranes.

Each membrane substrate is coated on one or both sides with a capture biomolecule, such as an antibody, such that it may specifically bind a target biomolecule, such as a protein. Antibodies acting as capture biomolecules may be obtained from a variety of commercial sources or custom made by the user. For example, recombinant DNA technologies, peptide synthesis, or other techniques may be used by those skilled in the art.

The first step in producing the affinity membranes described herein is to create a surface amenable to the site-directed immobilization of biomolecules. Such a surface should contain functional groups that lend themselves to specific chemical interactions, such as chelation, coordination, ionic bonding, or covalent reaction. Primary amines are just such a functional group, as they are capable of each of the aforementioned chemical interactions. Therefore, any polymeric coating with primary amine groups would suffice. In the specific and non-limiting examples that accompany this application, chitosan and polyallylamine have served as the amine-functional polymer layer to which biomolecules are immobilized through site-directed chemical interactions.

However, it is often necessary to use a tie layer between the porous substrate and the amine-functional layer. By their nature, amine-functional polymers are soluble only in hydrophilic solvents, such as water, ethanol, or water/ethanol mixtures. Also by nature, porous substrates with the desired straight-through pore morphology are hydrophobic and cannot be wetted by the coating solution containing the amine-functional polymer. Tie layers, which are of an intermediate hydrophobicity/hydrophilicity, remedy this situation by creating a surface to which the amine-funtional layer can adhere. Polymers soluble in solvents slightly less hydrophilic than those used for the amine-functional polymer can serve as suitable tie layers. Such solvents include ethanol, isopropanol, and mixtures of these alcohols with low molecular weight ketones, such as acetone and methyl ethyl ketone, where the ketone makes up less than 50% of the mixture. In the specific and non-limiting examples that accompany this application, poly(vinyl acetate) (PVAc) and poly(vinyl butyral) (PVB) were used.

Figure 3:
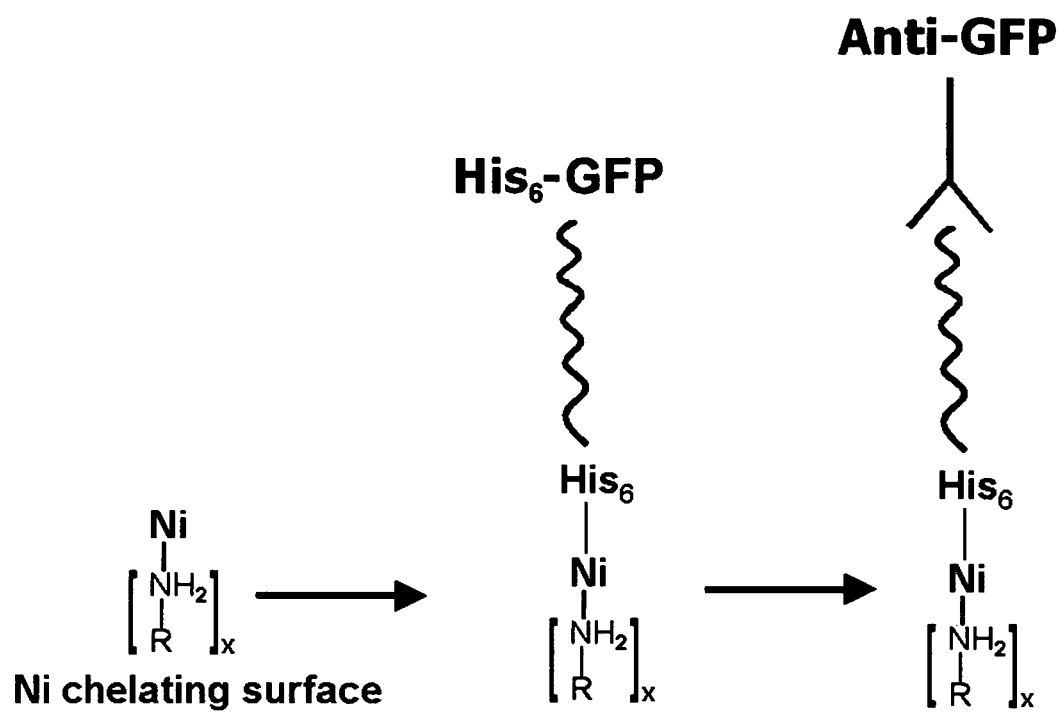
FIG. 3 illustrates the immobilization of his-GFP on a $Ni^{++}$-chelating surface.
Figure 12:
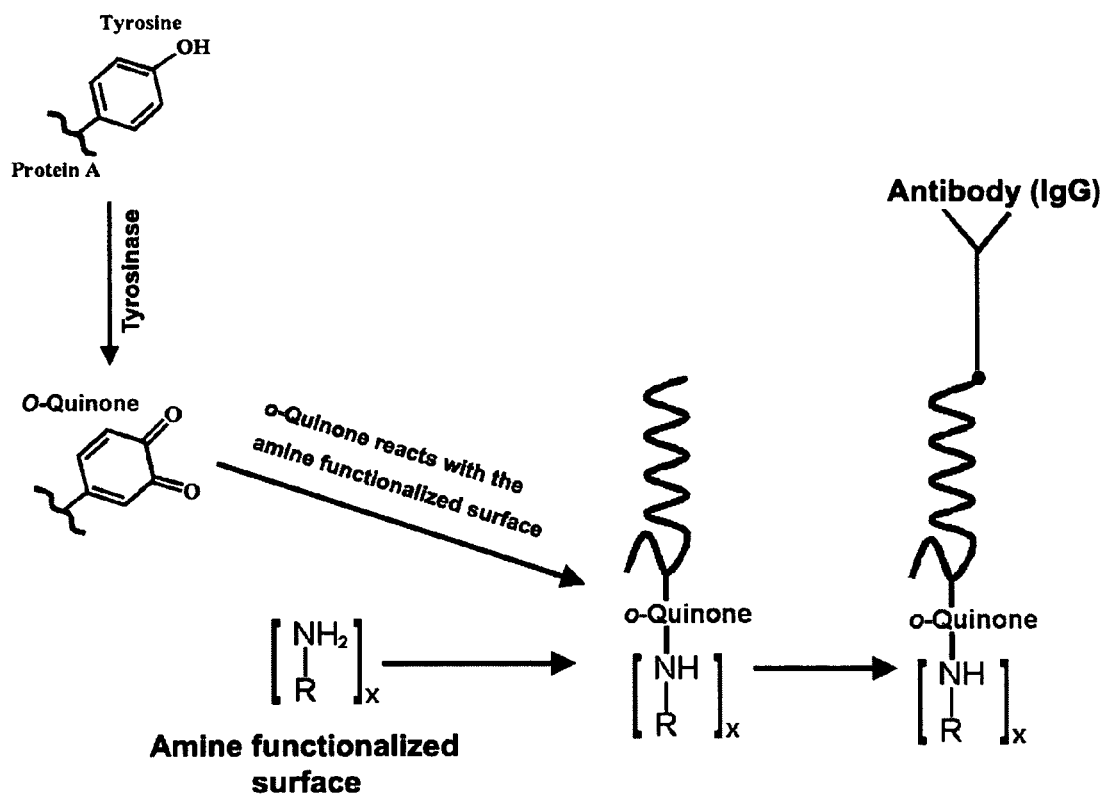
FIG. 12 illustrates antibody immobilization through binding to Protein A that has itself been immobilized through tyrosinase-catalyzed conversion of tyrosine to o-quinone.

With an amine-functional surface, chemical interactions between the amine groups and specific residues on a biomolecule can be used for the site-directed immobilization of that biomolecule. In the specific and non-limiting examples that accompany this application, two specific interactions were employed: (1) chelation between nickel ions, coordinated to the amine groups in a prior step, and histidine residues engineered to the terminal end of an alignment or capture biomolecule, and (2) enzyme-catalyzed reaction of tyrosine residues in an alignment of capture biomolecule to the amine groups. In Example (1), a histidine-tagged capture biomolecule (protein antigen) is immobilized for subsequent capture of target antibodies (FIG. 3). In Example (2), tyrosinase is used to catalyze the reaction between tyrosine residues on an alignment biomolecule (Protein A) and the amine groups (FIG. 12). The alignment biomolecule then binds to the capture biomolecule (antibody) for subsequent capture of target proteins.

Figure 2:
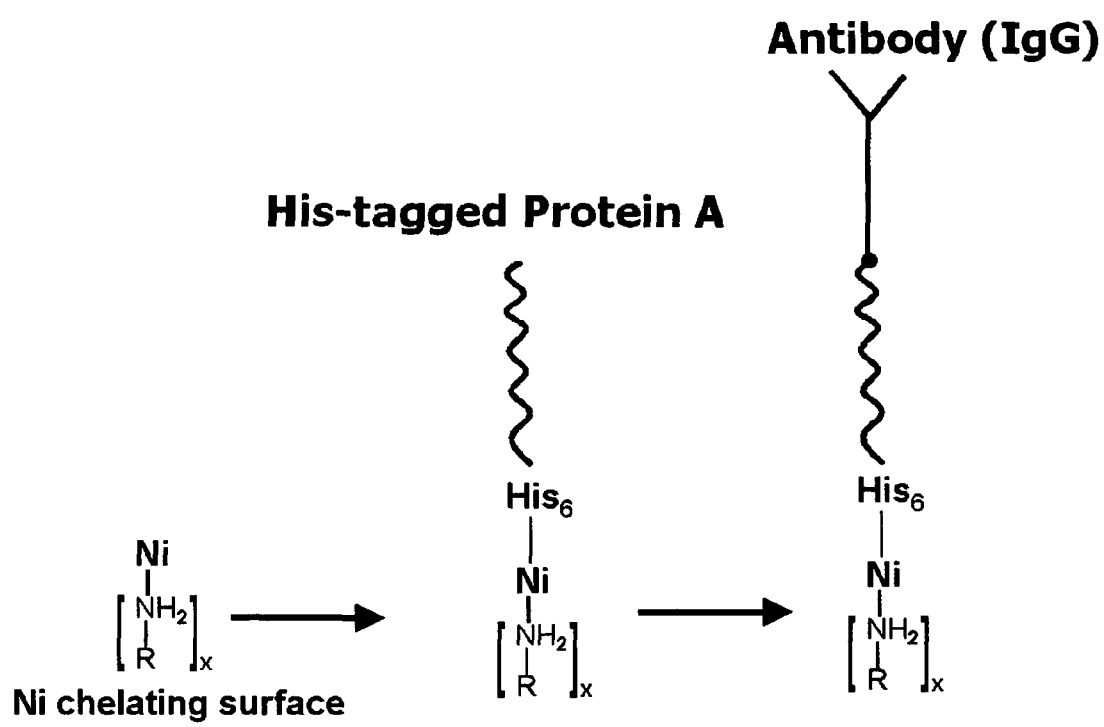
FIG. 2 illustrates antibody immobilization through binding to his-Protein A on a $Ni^{++}$-chelating surface.

In a variation of Example (1), a histidine-tagged alignment biomolecule can be immobilized to the Ni layer to which a capture biomolecule can be bound. For example, his-Protein A is first attached to the Ni layer, and then antibody is bound to the attached Protein A (FIG. 2). Alternatively, the antibody is first bound to the his-Protein A in a solution, whereupon the his Protein A-antibody pair will then be attached to the Ni. It should be noted that Protein A is not the only protein or material to which the antibodies can be attached and aligned. For example, Protein G could be used instead of Protein A. In fact, any proteinaceous material can be used that: (a) has the ability to bind and align an antibody, and (b) has a histidine tag which can form a chelation bond to the Ni while maintaining its physical and structural properties. More specifically, other proteins, besides Protein G, can be substituted for Protein A (actually just sub-units of the whole molecule) as long as the peptide sequence can bind to the Fc tail of the antibody. In fact, all Fc binding proteins and peptide sequences may be used provided histidine tagging is possible. Similarly, any protein antigen that can capture an antibody could be aligned by these methods.

Likewise in Example (2), it should be noted that Protein A is not the only protein or material to which the antibodies can be attached and aligned. In fact, any proteinaceous material can be used that (a) has the ability to bind and align an antibody and (b) has a tyrosine residue which can be transformed, using tyrosinase, into o-quinone and attached to the amine functional surface while maintaining its physical and structural properties. More specifically, other proteins, besides Protein G can be substituted for Protein A (actually just sub-units of the whole molecule) as long as the peptide sequence can bind to the Fc tail. In fact, all Fc binding proteins and peptide sequences may be used provided a tyrosine residue is present. Additionally, any protein antigen that can capture an antibody could be aligned by these methods.

The antibody orientation on the membranes and membrane stack can be used to detect and quantify antigens and antibodies in sera and other patient specimens for cancer detection, bacterial infection, and auto-immune diseases, and antibodies to virus titers A plurality of membranes or distinct locations on the membranes are each coated with an antibody, with each antibody having an affinity to a particular antigen or biomolecule and layered in a membrane stack. Test samples, preferably sera or saliva, are arranged in a multi-well grid or plate. The membrane stack is placed in contact with the grid or plate, and the samples travel through the membrane layers while maintaining their two-dimensional locations within the network. If present in a sample, target biomolecules, such as antigens, analytes or specific antibodies, are captured by their specific capture biomolecules as they pass through the membranes, and are subsequently detected using standard secondary antibody-based methods.

The Layered Antibody Array (LAA) can serve as a screening tool by detecting antigens, analytes, or other antibodies in a highly multiplexed format. Approximately 5,000 measurements per experiment are capable of being performed at one time. Indeed, this system and method may be used to screen for numerous diseases at one time using various biomarkers. Similarly, because antibodies are in more favorable orientations, a heightened sensitivity will exist that will allow for the earlier detection of prostate cancer, liver cancer, pancreatic cancer, and any other cancer or neoplastic cell condition that has an antigenic signature. Applied successfully, physicians can screen whole populations (or specific at-risk populations) for the presence or recurrence of a tumor as an adjunctive tool to current diagnostic techniques.

Similarly, the tests can measure antibodies that may be produced by the body against a physiological phenomena. This can be accomplished by attaching anti-antibodies to the membranes. Using the same methodology, sera samples can be screened for a panel of antigens or antibodies directed against toxic or infectious agents, or similarly, samples can be directed against antigens that are expressed as a result of toxic or infectious agents.

In FIGS. 10(a) and 11, test samples are arranged in a multi-well grid 16 (FIG. 10a) or wells 24 of the vacuum transfer manifold 25. It is preferred that there be a different test sample in each well, although at least one well may contain a positive control. Alternatively, there may be a negative control, or there may be both a positive control and a negative control, with the positive control containing proteins or antibodies that will be specific for each of the antibodies coating one of the membranes. The negative control can be a random assortment of proteins that should be specific for none of the antibodies.

The stack of membranes 12 is placed in contact with the wells. A blotting sheet (not shown) may be placed on top of the membrane stack 14. If present in a sample, proteins are specifically captured by their target antibody as they pass through the layers, and subsequently detected using standard secondary antibody-based methods. More specifically, proteins move from the multi-well grid and through the membranes via capillary action (or vacuum force), where they are captured by/bind to their corresponding antibodies. As the identity of the samples along the x-y plane of the biological sample platform (the array of samples in a multiwell plate or tissue section) are known, and the antibodies on the z-dimension representing the stack of capture membranes 14 are also known, determination of the positive sample is quick and easy, even without the use of a computer. With this approach, which may be referred to as a "layered antibody array" or "LAA"), multiple samples can be profiled or analyzed for multiple targets producing thousands of measurements in minutes.

In addition to the solutions listed above, tissue and cellular samples can also be tested for the presence of proteins or antibodies. Advantageously, when the samples are oriented in a two dimensional format such as with a standard multiwell (96, 384, or 1536 well) plates, 2-way multiplex analysis is enabled, wherein multiple samples may be simultaneously screened against multiple targets in parallel.

In a variation to the method given for use of the coated membranes, a membrane stack 12 may be used in conjunction with a multiwell vacuum transfer apparatus 20 (FIG. 11), with the vacuum 25 positioned underneath the membranes. As set forth herein, in lieu of a multiwell plate, membranes 14 may capture biomolecules from samples embedded in agarose gels.

The following are several non-limiting examples of uses and applications of the present disclosure.

1. Site-Directed Immobilization Through Histidine

Materials and Methods

Materials

Track-etched polycarbonate (PC) membranes (0.4 µm pore diameter, $1 \times 10^8$ pores/cm$^2$) were kindly provided by 20/20 GeneSystems, Inc. (Rockville, Md.). Chitosan, acetic acid, glutaraldehyde (25% aqueous), poly(vinyl acetate) (PVAc), nickel sulfate (NiSO$_4$), acetone (ACS grade) and ethanol (ACS grade) were purchased from Sigma-Aldrich (Milwaukee, Wis.). Sodium hydroxide (NaOH, 1M aqueous solution) and sodium borohydride (NaBH$_4$) were purchased from Fisher Scientific (Fairlawn, N.J.). Water (molecular biology grade), phosphate buffered saline (PBS) buffer (10× concentrate, molecular biology grade, pH=7.4), and Tris-HCl buffer (1M solution, pH=7.4, molecular biology grade) were purchased from Quality Biological (Gaithersburg, Md.). Green fluorescent protein (GFP) and Alexa Fluor 647 conjugated anti-green fluorescent protein antibody (antiGFP) were purchased from Molecular Probes (Eugene, Oreg.). Hexahistidine-tagged green fluorescent protein (his-GFP) was donated by Dr. W. E. Bentley of the University of Maryland, College Park. All reagents and proteins were used as received.

Surface Preparation of PC Membranes for Chitosan Coating

The PC membranes were first wetted with a 50/50 acetone/water mixture (by vol) and then dipped in a 0.2% (wt/vol) solution of PVAc in 50/50 acetone/ethanol (by vol). The membranes were placed on a flat surface and dried at room temperature for 1 h. PVAc coated membranes were then dipped in a 0.25% (wt/vol) solution of chitosan in 50/50 acetone/ethanol (by vol) at pH 3.5 (0.1% by volume acetic acid) and dried flat for 3 h at room temperature. The PVAc serves as a tie layer between the somewhat hydrophobic PC and the hydrophilic chitosan. The PC-chitosan composite membranes were subsequently dried in a 50° C. oven for 1 h. After drying, the membranes were washed in 1M sodium hydroxide (NaOH) to neutralize the protonated amine groups on the chitosan. The membranes were washed in 1× PBS solution for two periods of 5 min to remove excess NaOH. All of the membranes used in this study had dimensions of 2 cm×2 cm.

Formation of Ni$^{++}$-chelating Chitosan Layer

The PC-chitosan membranes described above were first stabilized against excessive swelling and possible dissolution during further processing by crosslinking in a solution of 0.1% (by vol) glutaraldehyde in 1× PBS for 1 h. The crosslinked PC-chitosan membranes were washed with 1× PBS to remove excess glutaraldehyde, treated with 0.2 M Tris-HCl buffer for 1 h to neutralize unreacted surface aldehyde groups, washed with a 0.25 mg/ml aqueous solution of NaBH$_4$ for 5 min to remove any Schiff base created during the amine-aldehyde reaction, and finally washed with deionized water to remove unreacted salts. A Ni$^{++}$-chitosan solution was prepared by dissolving 125 mg NiSO$_4$ in 100 ml of the chitosan solution described above. The membranes were then washed with 0.1% (by vol) acetic acid solution (pH 3.5) to compatibilize the crosslinked chitosan surface for the second chitosan coating, dipped in the Ni$^{++}$-chitosan solution, and then dried at room temperature for 3 h. After drying, the PC-chitosan-Ni$^{++}$ membranes were washed with NaOH for 10 min to neutralize the protonated amines in the chitosan and then washed with 1× PBS to remove unreacted NaOH.

Immobilization of His-GFP by Chelation to PC-chitosan-Ni$^{++}$ Membranes

PC-chitosan-Ni$^{++}$ membranes were washed with 1× PBS buffer for 10 min and incubated with 2 ml of 0.1 mg/ml his-GFP solution for 12 h at 4° C. After incubation, the membranes were washed twice with 1× PBS to remove unreacted his-GFP. Finally, the membranes were incubated in 0.1 mg/ml BSA solution (in 1× PBS) to block any sites that could result in the nonspecific binding of antiGFP in subsequent antibody binding experiments and then washed with 1× PBS buffer to remove excess BSA. FIG. 3 illustrates the his-GFP immobilization.

Immobilization of His-GFP by Glutaraldehyde Chemistry to PC-chitosan Membranes (Controls)

Figure 1:
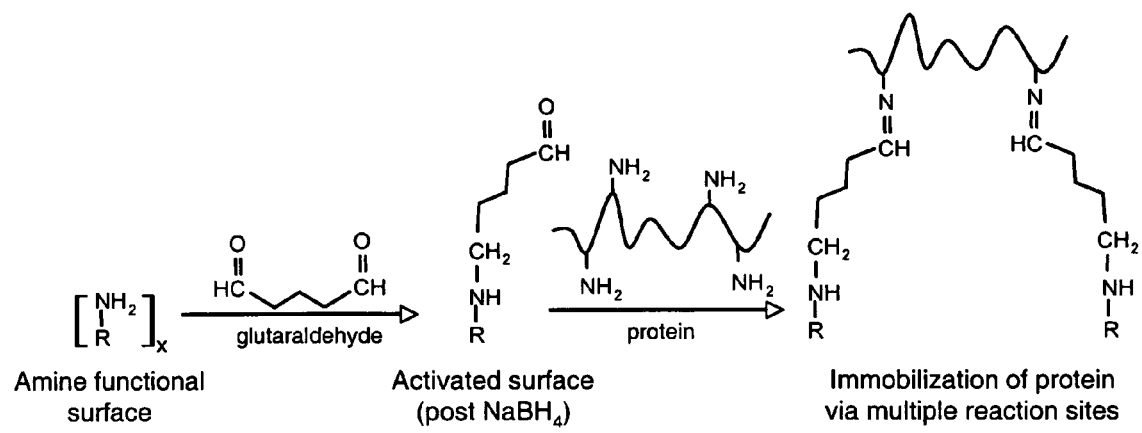
FIG. 1 illustrates the direct immobilization of protein using glutaraldehyde with an amine-functional surface.

PC-chitosan membranes were activated by washing them with a 0.1% (by vol) aqueous glutaraldehyde solution for 1 h. This step crosslinked the chitosan layer and also generated unreacted aldehyde groups for further reaction with the amine-functionalities in the his-GFP (FIG. 1). The activated membranes were subsequently washed in 1× PBS for 10 min to remove excess glutaraldehyde. The membranes were then washed with a 0.25 mg/ml aqueous solution of NaBH$_4$ for 5 min to remove any Schiff base created during amine-aldehyde reaction and washed with deionized water to remove unreacted salts. Glutaraldehyde activated membranes were incubated with 2 ml, 0.1 mg/ml his-GFP solution for 12 h at 4° C. The membranes were then washed with 0.2M Tris-HCl buffer and rinsed with 1× PBS to remove excess Tris-HCl buffer. The Tris-HCl buffer neutralized any unreacted active sites on the membrane surface. Finally, the membranes were incubated in 0.1 mg/ml BSA solution (in 1× PBS) to block any sites that could result in the nonspecific binding of antiGFP and then washed with 1× PBS buffer to remove excess BSA.

Fluorescence Scanning

Fluorescence scanning was used to investigate the extent of both his-GFP chelation and antiGFP binding. Membranes were scanned on a Typhoon™ scanner (Amersham Biosciences, Piscataway, N.J.). Signal intensity was determined by ImageQuant™ software (Amersham Biosciences, Piscataway, N.J.). AntiGFP binding intensity was normalized by dividing it by the intensity of the immobilized his-GFP:

$$I_N = \frac{I(antiGFP)}{I(GFP)} \quad (1)$$

Determination of Nonspecific Binding of GFP

In order to investigate the nonspecific binding of GFP to the $Ni^{++}$-chelating membrane, PC-chitosan-$Ni^{++}$ membranes were incubated in 2 ml, 0.1 mg/ml GFP, without the hexahistidine tag, for 12 h at 4° C. The membranes were then washed twice with 1× PBS to remove unbound GFP. In order to investigate nonspecific binding in the absence of $Ni^{++}$, PC-chitosan membranes were crosslinked with glutaraldehyde and neutralized with Tris-HCl as previously described. The PC-chitosan membranes were incubated in 2 ml, 0.1 mg/ml GFP solution for 12 h at 4° C. The membranes were then washed twice with 1× PBS to remove unbound GFP.

AntiGFP Binding

After his-GFP immobilization, PC-chitosan and PC-chitosan-$Ni^{++}$ membranes were washed with 2 ml of Alexa Fluor 647 conjugated antiGFP at concentrations ranging from 400 pg/ml to 5 µg/ml for 15 min at 4° C. The membranes were then washed twice with 1× PBS buffer to remove excess antiGFP, and placed on clean glass slides to facilitate fluorescence scanning. The membranes on the slides were dried and stored in the dark at 20° C. until scanning. During antiGFP binding, solution concentrations remained unchanged, within experimental error.

Membrane Surface Characterization

An ElectroScan E-3 environmental scanning electron microscope (ESEM) was used to investigate the surface porosity of PC-chitosan-$Ni^{++}$ membranes. X-ray photoelectron spectroscopy (XPS) spectra of the PC-chitosan-$Ni^{++}$ membrane surfaces were obtained with a Kratos AXIS 165 spectrometer with Al KR X-ray source (1486.6 eV). Survey spectra (resolution of 1 eV) and high-resolution spectra (resolution of 0.05 eV) of the C1s, O1s, N1s, and Ni2p bands were obtained.

Results and Discussion

PC-chitosan-$Ni^{++}$ Membranes Retain Open Pores after Formation

The formation of a $Ni^{++}$-chelating membrane required the use of two compatibilizing tie layers between the track-etched PC base membrane and the chitosan-$Ni^{++}$ active layer. The chitosan-$NiSO_4$ solutions are unable to wet the base PC membranes directly. The first tie layer, PVAc, is of intermediate hydrophobicity/hydrophilicity. The second tie layer is chitosan, which is crosslinked to prevent excessive swelling or dissolution during the application of the chitosan-$NiSO_4$ solution (pH 3.5). With the application of three layers on the base PC, it is important to insure that the membranes retain their porosity for layered multimembrane blotting. ESEM images of the base membrane (PC) and of a PC-chitosan-$Ni^{++}$ membrane are shown in FIG. 4. The ESEM images indicate that the PC-chitosan-$Ni^{++}$ membrane retained its porosity and the coating process did not affect the uniformly-distributed, isolated pore structure of the track-etched PC base membrane.

$Ni^{++}$ is Coordinated with the Functional Groups of Chitosan

Figure 5:
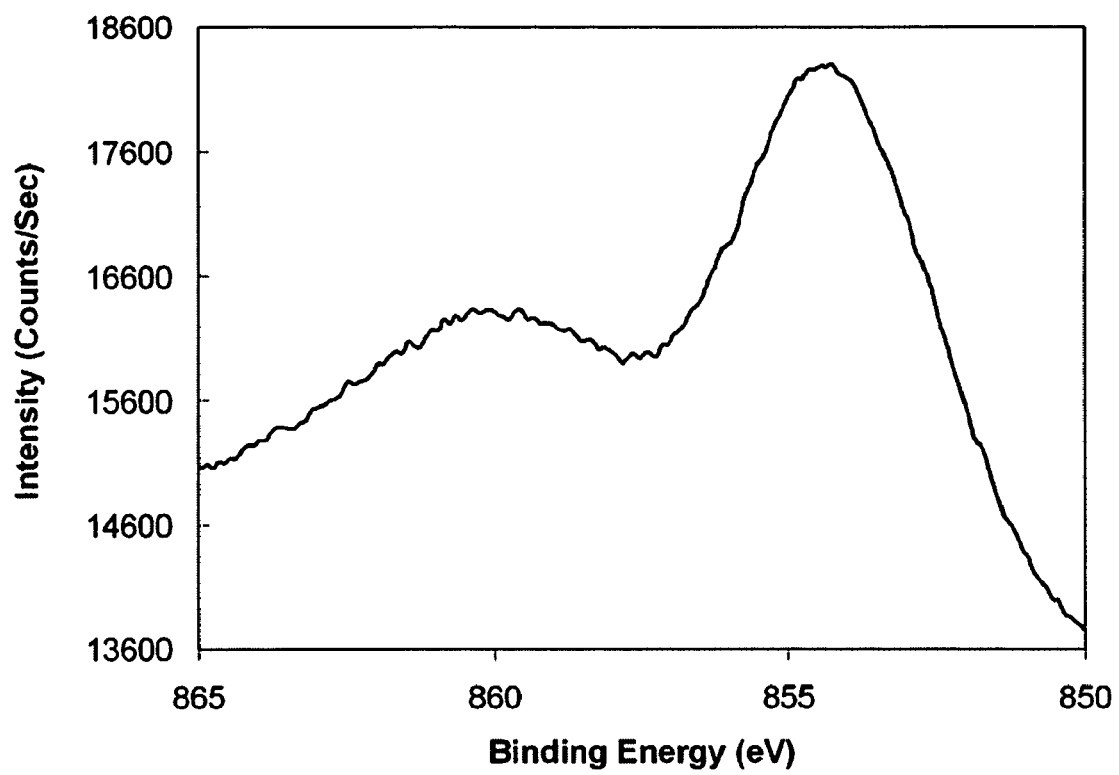
FIG. 5 is a graph showing the $Ni2p_{3/2}$ peak from XPS of PC-chitosan-$Ni^{++}$ membrane.

XPS was used to study the $Ni^{++}$ coordination to functional groups in chitosan (—OH and —$NH_2$). The $Ni2p_{3/2}$ high-resolution spectrum is shown in FIG. 5. The main $Ni2p_{3/2}$ peak occurred at 854.26 eV, and had a satellite peak at 860.05 eV. This spectrum is very similar to that obtained from the $Ni^{++}$-NTA(nitrilotriacetic acid) complex often used in IMAC. An elemental analysis calculated from the XPS spectrum indicates that the ratio of N:Ni is 4:1, which is consistent with the ratio used in the chitosan-$NiSO_4$ coating solution.

Figure 6:
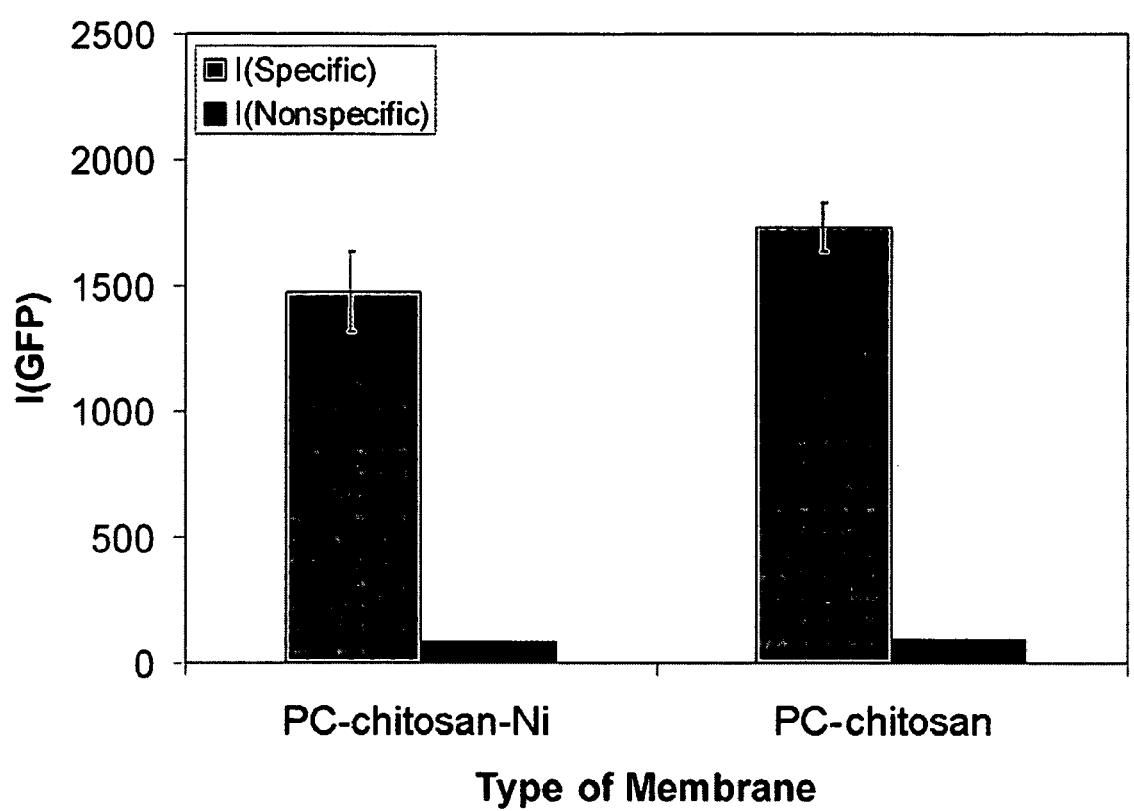
FIG. 6 is a graph showing a comparison of immobilized (specific) his-GFP (green intensities at 4° C. (n=3). PC-chitosan-Ni and PC-chitosan refer to immobilization through Ni$^{++}$ chelation and glutaraldehyde chemistry, respectively. Nonspecific GFP (no his tag) adsorption on each membrane type from a single experiment.

PC-chitosan-$Ni^{++}$ Membranes Chelate His-GFP with Minimal Nonspecific Binding Fluorescence scanning indicates that his-GFP was successfully immobilized by chelation to the surface of PC-chitosan-$Ni^{++}$ membranes (FIG. 6). FIG. 6 also shows his-GFP immobilized to the surface using glutaraldehyde, as a control, for comparison. The PC-chitosan-$Ni^{++}$ membranes have nearly the same amount of his-GFP on the surface as the PC-chitosan controls, on the basis of fluorescence intensity. The amount of nonspecific binding is within the error of the intensity measurement for the specific binding membranes ($Ni^{++}$ chelation or glutaraldehyde chemistry).

Figure 7:
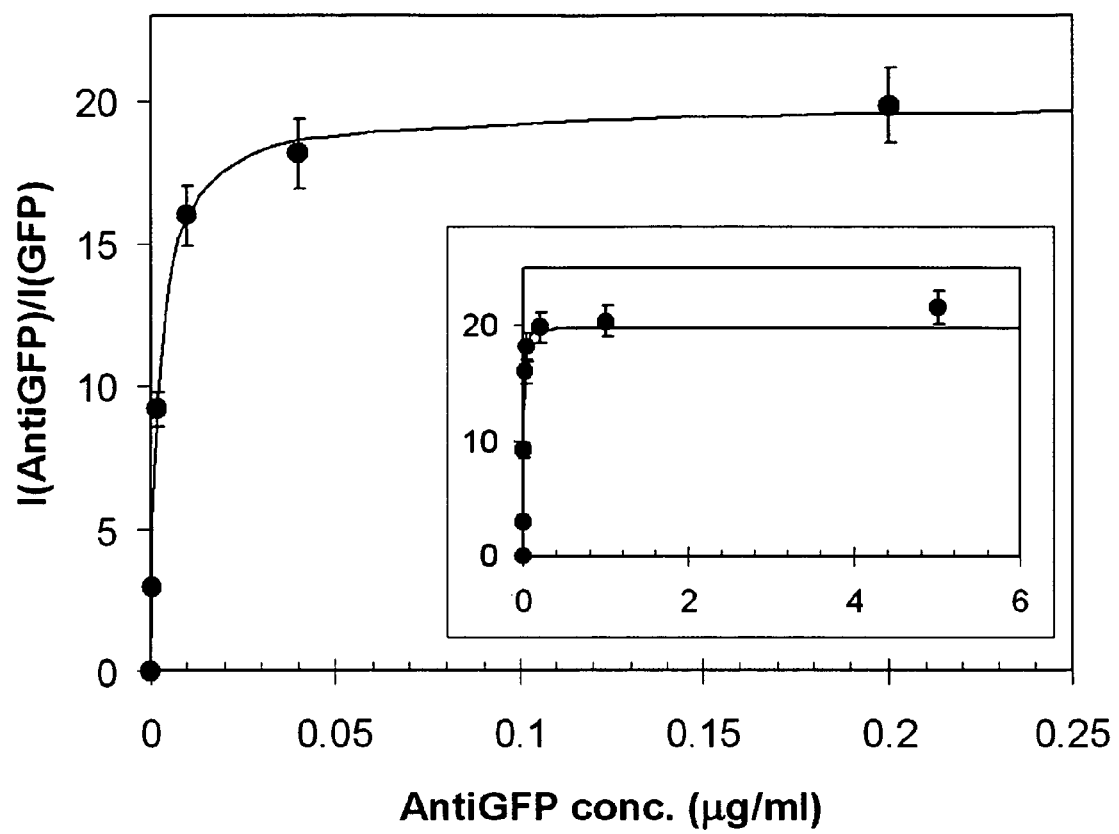
FIG. 7 is a graph showing the adsorption isotherm at 4oC for antiGFP binding to his-GFP immobilized to PC-chitosan-Ni$^{++}$ membranes (n=3 at each concentration); The line represents the single-site Langmuir model fit of the data (C<0.25 μg/ml)
Figure 8:
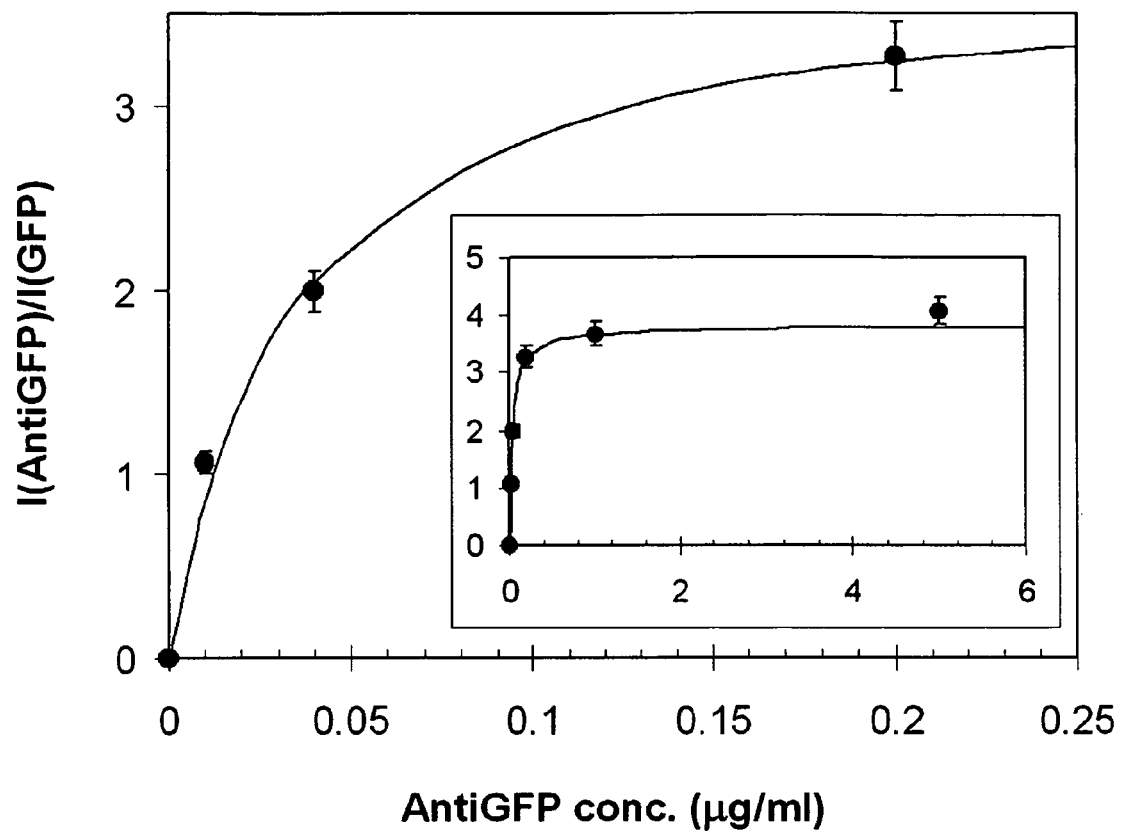
FIG. 8 is a graph showing the adsorption isotherm at 4° C. for antiGFP binding to his-GFP directly immobilized using glutaraldehyde to PC-chitosan membranes (n=3 at each concentration). The line represents the single-site Langmuir model fit of the data (C<0.25 μg/ml)

His-GFP Chelated to $Ni^{++}$ is more Biologically Active than Glutaraldehyde-immobilized his-GFP Although PC-chitosan-$Ni^{++}$ and PC-chitosan have similar his-GFP surface concentrations, it was hypothesized that controlling the orientation of his-GFP through $Ni^{++}$ chelation would result in both higher capacities and higher affinities for antiGFP binding compared to the PC-chitosan control. Isotherms for antiGFP binding to his-GFP are shown in FIGS. 7 and 8 for PC-chitosan $Ni^{++}$ and PC-chitosan, respectively. The data were fit with a single-site Langmuir model:

$$I_N = \frac{I_N^{sat} bC}{1 + bC} \quad (2)$$

where $I_N$ is the normalized antiGFP binding, $I_N^{sat}$ represents the normalized binding at saturation, b is the affinity of antiGFP toward his-GFP, and C is the antiGFP concentration in solution. The results of the fits are summarized in Table 1. From FIGS. 7 and 8 (and Table 1), it can be seen that at low concentrations (C<0.25 µg/ml), normalized antiGFP binding intensity is well represented by the single-site Langmuir model. At higher concentrations (C>0.25 µg/ml), antiGFP binding deviates slightly from the single-site Langmuir model predictions. This may be the result of minor amounts of multilayer binding (antibody-antibody interactions).

TABLE 1

Fitting parameters for the single-site Langmuir model for antiGFP binding to surface-immobilized his-GFP at 4° C.

| Membrane | $I_N^{sat}$ | b (ml/µg) | $R^2$ (C < 0.25 µg/ml) |
|---|---|---|---|
| PC-chitosan-$Ni^{++}$ | 19.8 | 410 | 0.998 |
| PC-chitosan | 3.8 | 29 | 0.993 |

The values of $I_N^{sat}$ (Table 1) indicate that the use of $Ni^{++}$-chelating groups results in a 5-fold enhancement in the binding capacity (number of active sites) for the target antiGFP. Random his-GFP orientations likely occur during direct immobilization with glutaraldehyde with multiple reaction sites (crosslinking) possible for some of the his-GFP. The chelation of the histidine tag to $Ni^{++}$ results in more protein being available for antibody binding. The affinity, b, of anti-GFP for his-GFP on PC-chitosan-$Ni^{++}$ membranes is 14 times higher than that on the PC-chitosan control. This suggests that the glutaraldehyde-immobilized his-GFP molecules that are actually available for antibody binding may not be in the most favorable orientation. Since glutaraldehyde can link the his-GFP through any amine-functionality, there is likely a random distribution of his-GFP orientations using this immobilization technique. In contrast, $Ni^{++}$-chelated his-GFP is linked to the surface only at the C-terminus, resulting in a single orientation that results in a stronger interaction with the binding antibody. FIG. 9 schematically depicts the differences between the two methods of his-GFP immobilization, showing how both the capacity and affinity for anti-GFP binding are improved through orientation control. At very low concentrations (bC<<1), the isotherm is linear and at a given concentration, the $Ni^{++}$-chelated his-GFP binds 70 times more antibody than the control, resulting in nearly 2 orders of magnitude higher sensitivity.

Conclusions

Affinity membranes based on the chelating ability of $Ni^{++}$ to terminal histidine tags in engineered proteins were developed for use in multimembrane blotting applications. The $Ni^{++}$ was introduced to the surface through its ability to coordinate with amine-functional polymers. Track-etched polycarbonate served as the base membrane, which was surface modified for the chitosan-$Ni^{++}$ functional layer using compatibilizing tie layers. The immobilization of histidine-tagged GFP through $Ni^{++}$ chelation resulted in a surface with both enhanced capacity and affinity for binding a target antibody relative to immobilization through glutaraldehyde chemistry. The results of this work should be extendable to the immobilization of any histidine-tagged protein. One application of particular interest is the immobilization of histidine-tagged Protein A or Protein G on a $Ni^{++}$-chelating surface. With the ability of antibodies to bind to Protein A or G through their Fc fragments, the membranes described in this work should be able to orient an antibody such that its Fab fragments are accessible for binding target protein antigens. The ability to capture specific proteins with their respective antibodies would be highly advantageous to any assay based on the identification of biomarker proteins.

2. Site-Directed Immobilization Through Tyrosine

Materials and Methods

Materials

Track-etched polycarbonate (PC) membranes (0.4 μm pore diameter, $1 \times 10^8$ pores/cm$^2$) were obtained from 20/20 GeneSystems, Inc. (Rockville, Md.). Tyrosinase from mushroom, Protein A from *Staphylococcus aureus*, polyallylamine (25 wt.% in water), polyoxyethylene sorbitan monolaurate (Tween®20), acetic acid, glutaraldehyde (25 wt.% in water), and ethanol (ACS grade) were purchased from Sigma-Aldrich (Milwaukee, Wis.). Alexa Flour 647 conjugated Protein A (AF647-Protein A) from Staphylococcus aureus, FITC conjugated IgG (FITC-IgG), Alexa Flour 647 conjugated bovine serum albumin (AF647-BSA), green fluorescent protein (GFP), polyclonal anti-bovine serum albumin IgG (antiBSA, rabbit IgG fraction) and anti-green fluorescent protein IgG (antiGFP, rabbit IgG fraction) were purchased from Molecular Probes (Eugene, Oreg.). Poly(vinyl butyral) (19% hydroxyl) was purchased from Scientific Polymer Products, Inc. (Ontario, N.Y.). Sodium borohydride ($NaBH_4$) was purchased from Fisher Scientific (Fairlawn, N.J.). Water (molecular biology grade), phosphate buffered saline (PBS) buffer (10× concentrate, molecular biology grade, pH=7.4), Tris buffered saline (TBS) buffer (10× concentrate, molecular biology grade, pH=7.4), and Tris-HCl buffer (1M solution, pH=7.4, molecular biology grade) were purchased from Quality Biological (Gaithersburg, Md.). TBST buffer was prepared by adding 5 ml Tween®20 to 1000 ml 1× TBS buffer.

Surface Preparation of PC Membranes for Polyallylamine (PAA) Coating

The PC membranes used in this study are somewhat hydrophobic and cannot be wetted with an aqueous polyallylamine (PAA) solution. In order to obtain a uniform PAA coating, it was necessary to modify the membrane surface with a coating of intermediate hydrophilicity that can act as a tie layer between the PC and PAA. A proper tie layer for PAA must meet two key criteria: (i) it should be water insoluble, as PAA is water soluble and any water soluble tie layer will swell excessively or dissolve during PAA coating, and (ii) it must be soluble in a solvent that can wet the surface of PC without affecting the structural integrity of the membrane. Poly(vinyl butyral) (PVB) was chosen here as it satisfied these criteria. It is water insoluble, yet soluble in ethanol, which wets the PC surface well without excessive swelling or distortion of the base membrane.

A 0.2% (wt/vol) PVB solution was prepared by dissolving the polymer in ethanol. A 0.5% (wt/vol) PAA solution was prepared by dilution of the purchased 20 wt% PAA aqueous solution in a 50/50 mixture (by vol) of ethanol and deionized water. The PC membranes were wetted with ethanol, dipped in the PVB solution, and dried at 4° C. in an enclosed chamber filled with ethanol vapor. PVB coated membranes were then wetted with a 50/50 water/ethanol solution (by vol) and dipped in the PAA solution. The PC-PAA membranes were dried in an enclosed chamber filled with ethanol/water vapor at 4° C. The vapor-saturated, enclosed chambers were used in both of these steps to control the rate of solvent evaporation and thereby insure smooth coatings.

Immobilization of Protein A on PC-PAA Membranes using Glutaraldehyde Chemistry

PC-PAA membranes were activated by washing them with a 0.1 wt% aqueous glutaraldehyde solution for 1 h. This washing step crosslinked the PAA layer and also generated unreacted aldehyde groups for further reaction with Protein A (FIG. 1). The activated membranes were subsequently washed in 1× PBS buffer for 10 min to remove excess glutaraldehyde. The membranes were then washed with a 0.25 mg/ml aqueous solution of $NaBH_4$ for 5 min to remove any Schiff base created during amine-aldehyde reaction and washed with deionized water to remove unreacted salts. Glutaraldehyde(g)-activated membranes were incubated with 100 μg/ml Protein A solutions for 12 h at 4° C. The resulting PC-PAA-(g)Protein A membranes were then washed with 0.2M Tris-HCl buffer to neutralize any unreacted aldehyde on the membrane surface. Finally, the membranes were rinsed with 1× PBS to remove excess Tris-HCl buffer.

Immobilization of Protein A on PC-PAA Membranes through Tyrosinase Catalyzed Reaction The PC-PAA membranes were crosslinked by washing them with a 0.1 wt% aqueous glutaraldehyde solution, treated with 0.2 M Tris-HCl buffer, washed with a 0.25 mg/ml aqueous solution of $NaBH_4$, and then washed in deionized water, as described above. These crosslinked and neutralized PC-PAA membranes were used to immobilize Protein A using tyrosinase catalyzed reaction to the amine groups on PAA. Tyrosinase was added to Protein A solutions and the PC-PAA membranes were incubated for 12 h at 4° C. The amount of tyrosinase added was varied to determine the optimal amount for maximum IgG binding to the immobilized Protein A. Tyrosinase converts the phenolic group of a tyrosine (tyr) residue on Protein A into an o-quinone, which then reacts with a primary amine on PAA to immobilize the Protein A on the membrane surface (FIG. 12). After reaction, the PC-PAA-(tyr)Protein A membranes were washed twice with 1× PBS buffer for 10 min to remove unreacted Protein A from the membrane.

Antibody Binding to Protein A Immobilized PC-PAA Membranes

IgG binding experiments were performed to determine the extent of antibody binding to Protein A for both types of immobilization techniques (PC-PAA-(g)Protein A and PC-PAA-(tyr)Protein A). Immediately upon AF647-Protein A immobilization, the membranes were washed with 1× casein solution at 4° C. to block unreacted sites on the surface of the membranes and to minimize nonspecific binding. The membranes were washed with 2 ml, FITC-IgG at different concentrations (5 ng/ml-40 μg/ml) for 15 min at 4° C. The membranes were then washed twice with 1× PBS buffer to remove excess IgG. FITC-IgG conjugated membranes were placed on clean glass slides and stored in the dark at 20° C. until scanning.

For the protein capture experiments, unlabelled Protein A was used and the membranes were washed with 2 ml of a 20 μg/ml antibody solution (either antiBSA or antiGFP) for 15 min at 4° C. The membranes were then washed twice with 1× PBS buffer to remove excess antibody and immediately used for protein capture experiments.

Protein Capture by Immobilized Antibodies on Layered PC-PAA Membranes

Figure 13:
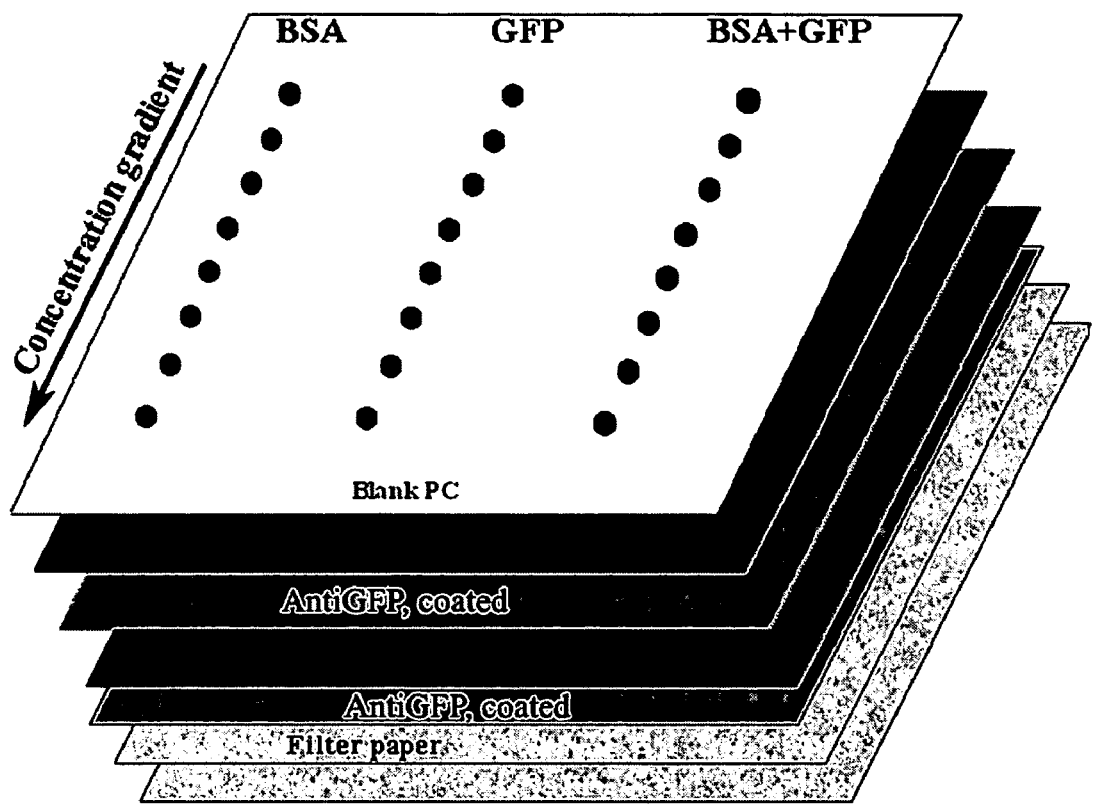
FIG. 13 is a schematic illustration of layered affinity membranes for specific protein capture as a function of protein concentration. The layers are numbered 1-4 from the top (closest to dot blot) down.

Four-layer membrane stacks, using either PC-PAA-(tyr) Protein A-IgG or PC-PAA-(g)Protein A-IgG membranes, were prepared by placing two antiBSA and two antiGFP membranes (wetted with 1× PBS) alternatively on top of each other (see FIG. 13). One wetted PC membrane was placed on top of the stacks. The membrane stacks were then placed on 1× PBS wetted filter paper. To demonstrate the specific protein capture ability of the membranes, the stacks were spotted with 2 μl solutions of AF647-BSA, GFP and a 50/50 (by wt) mixture of the two at various amounts of total protein (2.5 ng-500 ng). After 10 minutes, the membranes were washed twice with 1× TBST buffer for 10 minutes to remove nonspecifically bound proteins and placed on glass slides for scanning.

Protein Binding Isotherm and Binding Kinetics

Since samples are drawn rapidly through the porous membranes during dot blotting and capillary transfer, the specific capture of a protein is a dynamic binding event. In order to investigate the time scale for protein binding, antiBSA-coupled membranes were incubated in AF647-BSA at a concentration of 1 μg/ml for various times at 4° C. The equilibrium binding isotherm was determined by incubating in AF647-BSA solutions at various concentrations (5 ng/ml-0.1 mg/ml) for 1 h at 4° C. In all binding experiments, the membranes were washed twice with 1× TBST buffer for 10 min to remove nonspecifically bound BSA and placed on glass slides for scanning.

Fluorescence Scanning

Fluorescent detection was used to investigate the intensity of protein binding. Membranes were scanned using a Typhoon™ scanner (Amersham Biosciences, Piscataway, N.J., USA). The fluorescence intensity was determined using ImageQuant™ software (Amersham Biosciences, Piscataway, N.J., USA).

Scanning Electron Microscopy (SEM)

An ElectroScan E-3 environmental scanning electron microscope (ESEM) was used to investigate the surface characteristics of PC-PAA membranes. The pore size distribution was deteremined from the ESEM images using Scion Image 4.02 image analysis software.

Results and Discussion

PC-PAA Membranes Retain Open Pores

Figure 14:
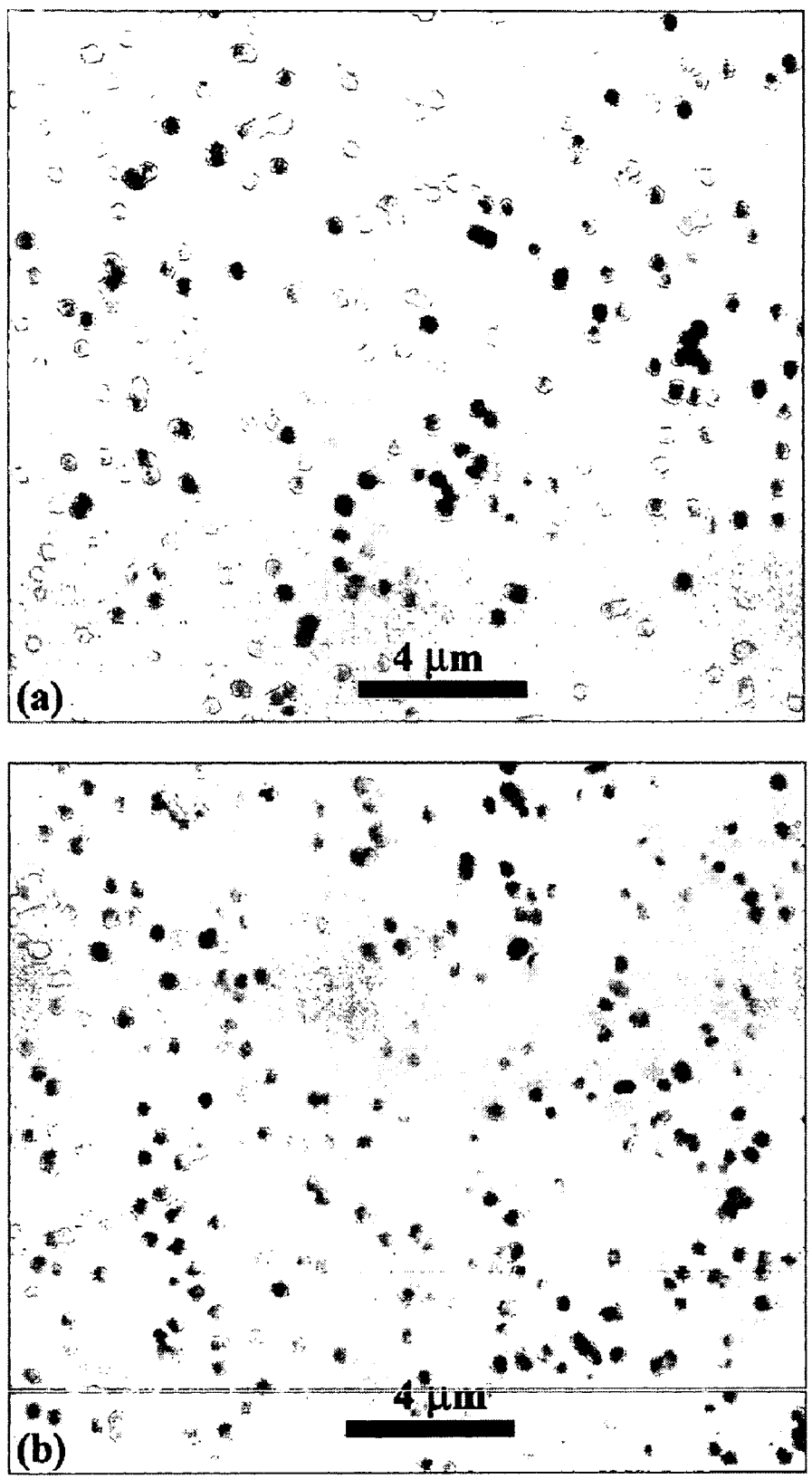
FIG. 14 is a monograph of SEM images of (a) PC and (b) PC-PAA membranes, showing that the PAA coating does not block the pores of the base membrane.

Environmental scanning electron microscopy (ESEM) was used to verify that the porosity of the PC membranes was maintained upon PAA coating. ESEM images of the base PC and PC-PAA membranes are shown in FIG. 14 and indicate that both the porosity and the uniformly-distributed, isolated pore structure are retained in the PC-PAA membranes. However, a very slight decrease in the mean pore size was observed after PAA coating. The pore radii of the base PC and PC-PAA membranes were 0.19±0.02 μm and 0.18±0.02 μm, respectively.

Optimal Conditions for Protein A Immobilization via Tyrosinase-catalyzed Reaction The tyrosinase to Protein A ratio must be optimized such that multiple tyrosine residues per protein chain do not react with the membrane surface or with each other and, in turn, reduce the bioactivity towards binding IgG. A number of experiments were performed to determine the lowest tyrosinase activity and the lowest Protein A concentration necessary for optimal IgG surface coverage of the membrane. In each experiment, the enzymatic reaction was carried out for 12 h at 4° C. In the first set of experiments, the Protein A concentration was held constant at 100 μg/ml while the tyrosinase activity was varied from 1.25 to 400 U μg-Protein A. In the second set of experiments, the tyrosinase to Protein A ratio was fixed at the optimal value from the first set of experiments and the Protein A concentration was varied.

Figure 15:
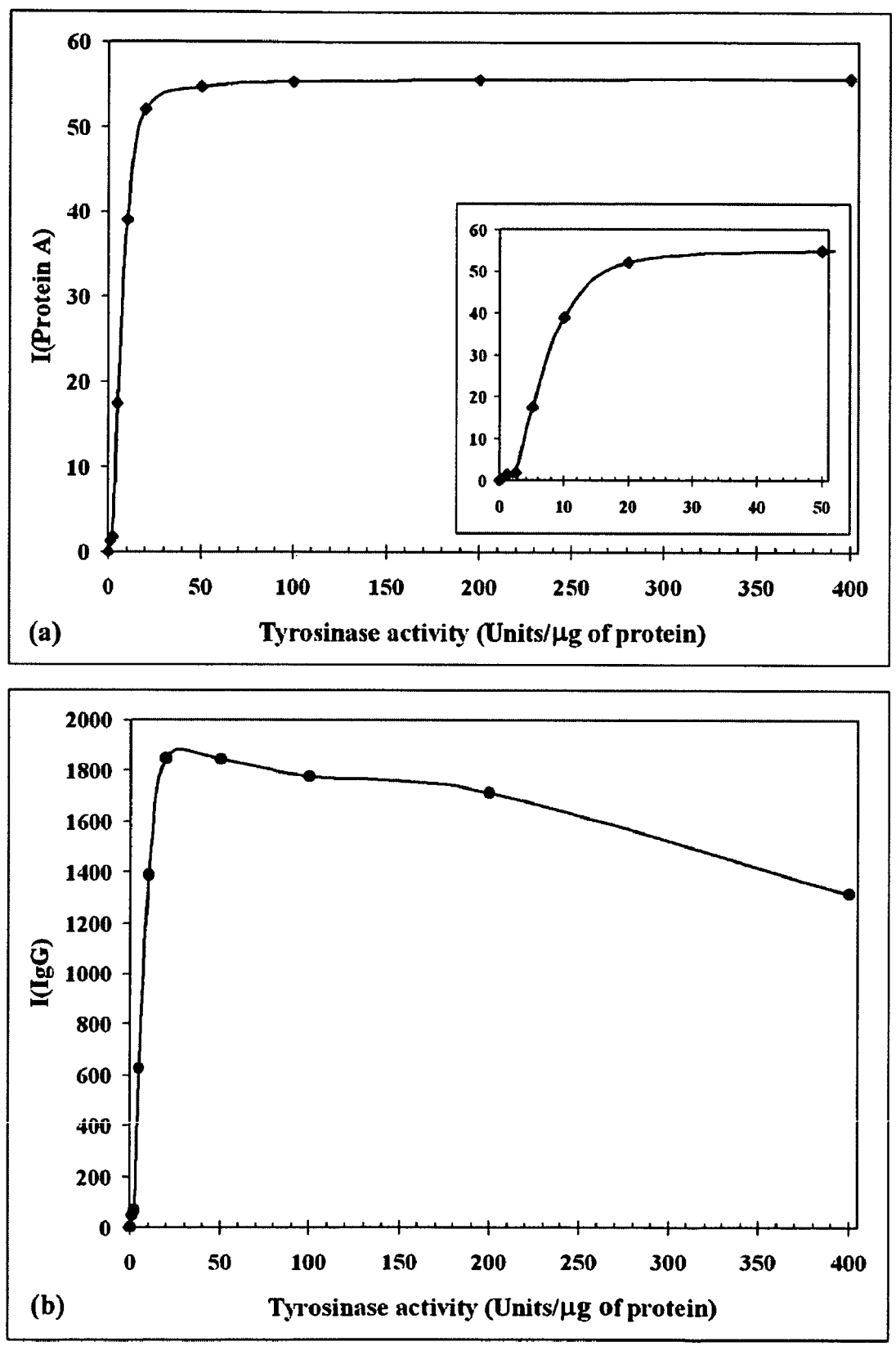
FIG. 15 is a graph showing the effect of tyrosinase activity on (a) immobilization of Protein A, and (b) IgG binding by immobilized Protein A.

From the first set of experiments, at tyrosinase activities less than 2.5 U/μg-Protein A, there was little measurable Protein A or IgG on the surface (FIG. 15). Between activities of 2.5 and 20 U/μg-Protein A, there was a monotonic increase in the amount of attached Protein A with an expected proportional increase in bound IgG (1:1 antigen/antibody interaction). At activities greater than 20 U/μg-Protein A, the amount of attached Protein A was independent of tyrosinase activity (surface saturation), but the amount of bound IgG decreased slightly with increasing activity. This loss in IgG binding ability suggests that Protein A orientation may be compromised at higher enzyme activities owing to either the reaction of multiple tyrosines per protein to the surface amine groups or the reaction of tyrosines in one molecule of Protein A to pendant amine groups in another (crosslinking). To minimize the probability of surface immobilization through multiple reaction sites or crosslinking, an activity of 20 U/μg-Protein A was used for the second set of experiments.

Figure 16:
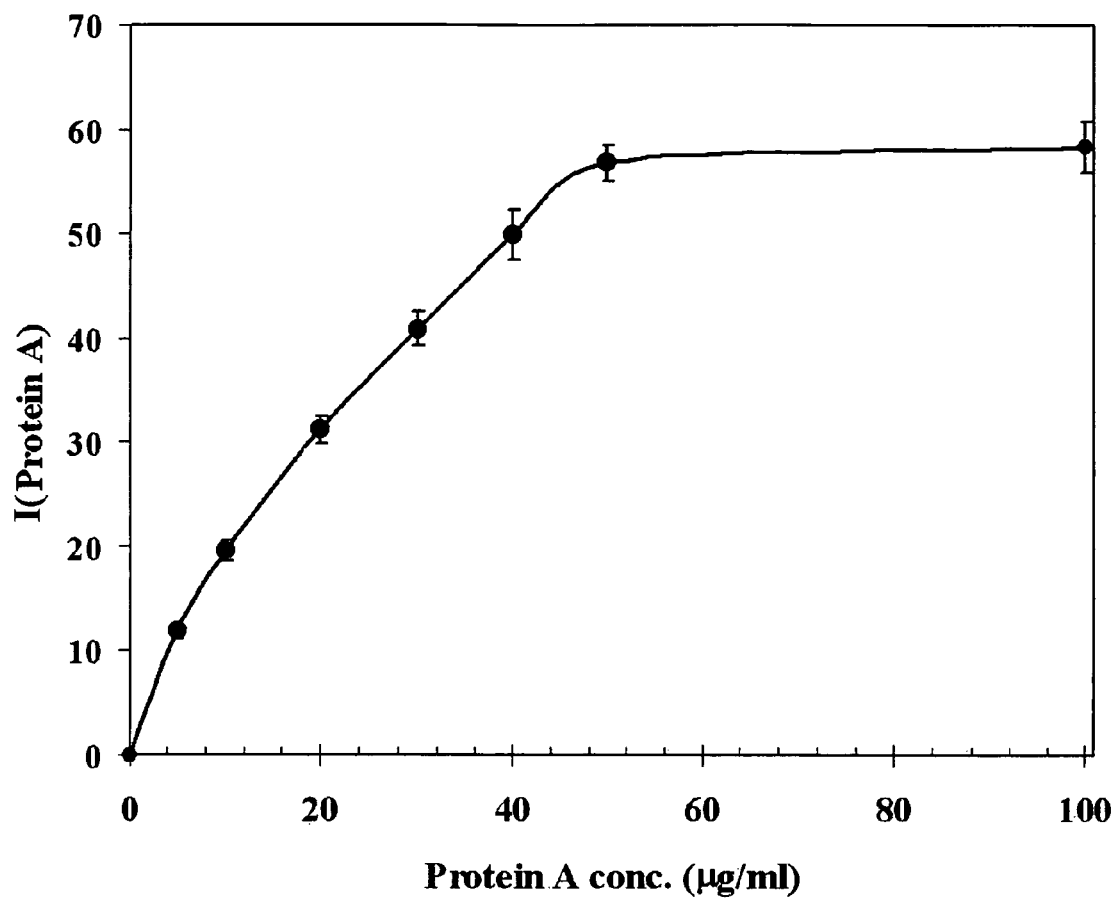
FIG. 16 is a graph showing the effect of Protein A concentration on tyrosinase-catalyzed immobilization.

Fixing the tyrosinase activity at 20 U/μg-Protein A, the concentration of Protein A was varied from 5 to 100 μg/ml. The amount of Protein A immobilized to the membrane surface increased with an increase in Protein A concentration up to 50 μg/ml, above which there was essentially no change (FIG. 16). For all subsequent IgG binding experiments, the tyrosinase-catalyzed immobilization of Protein A was done at a Protein A concentration of 50 μg/ml and a tyrosinase activity of 20 U/μg-Protein A. It should be noted that tyrosinase/

Protein A solutions that are not used within 24 hours of preparation result in lowered amounts of IgG surface coverage. Although the reaction of o-quinones is highly selective towards the primary amines on the surface, there can be some protein-protein coupling at long times in solution.

Isotherms for IgG Binding to Immobilized Protein A

The IgG binding isotherms for PC-PAA-(tyr)Protein A and PC-PAA-(g)Protein A membranes were determined by investigating the amount of IgG bound as a function of solution concentration (FIG. 17). IgG binding intensity was normalized to the intensity of Protein A on the membrane surface, $I_N = I_{IgG}/I_{Protein\,A}$. The IgG binding characteristics were evaluated by fitting the data to single-site and two-site Langmuir models, given by equations 2 (repeated from above for sake of clarity) and 3, respectively:

$$I_N = \frac{I_N^{sat} bC}{1 + bC} \quad (2)$$

$$I_N = \frac{I_{N1}^{sat} b_1 C}{1 + b_1 C} + \frac{I_{N2}^{sat} b_2 C}{1 + b_2 C} \quad (3)$$

In these equations, $I_N$ and C are the measured fluorescence intensity for the bound BSA and the BSA solution concentration, respectively, $I_N^{sat}$ is the binding capacity, and b is the binding affinity.

From FIG. 17a, it can be seen that at low concentrations (C<0.5 μg/ml), normalized IgG binding intensity follows a single-site model well for tyrosinase-immobilized Protein A. Since the Langmuir framework assumes that sites of a particular affinity are equivalent, the lack of a stronger correlation at low concentrations for IgG binding to glutaraldehyde-immobilized Protein A is not surprising (FIG. 17b). However, the resulting affinity parameter can still be useful for comparison with that for the tyrosinase-immobilized Protein A. At higher concentrations, IgG binding deviates from the single-site model and better follows the two-site model. The parameter values are listed in Tables 2 and 3 for the single-site and two-site models, respectively.

TABLE 2

Fitting parameters for a single-site Langmuir model for IgG binding to surface-immobilized Protein A at 4° C.

| Membrane | $I_N^{sat}$ | b (ml/μg) |
|---|---|---|
| PC-PAA(tyr)-Protein A | 9.85 | 143 |
| PC-PAA(g)-Protein A | 0.35 | 1.25 |

TABLE 3

Fitting parameters for a two-site Langmuir model for IgG binding to surface-immobilized Protein A at 4° C.

| Membrane | $I_{N1}^{sat}$ | $b_1$ (ml/μg) | $I_{N2}^{sat}$ | $b_2$ (ml/μg) |
|---|---|---|---|---|
| PC-PAA(tyr)-Protein A | 9.85 | 143 | 4.73 | 0.60 |
| PC-PAA(g)-Protein A | 0.35 | 1.25 | 0.22 | 0.11 |

The parameters calculated from the two-site model show two distinct binding affinities, one high and one low. The high-affinity constant ($b_1$) is more than two orders higher than the low-affinity constant ($b_2$) for PC-PAA-(tyr)Protein A, while the two affinity constants differ by one order of magnitude for PC-PAA-(g)Protein A. This may be explained by taking into account the structure of IgG. IgG is typically depicted as a Y-shaped molecule (FIG. 12) with two Fab fragments forming an antigen binding site at the top and an Fc tail that has a very high affinity towards Protein A. Physically, the high affinity constant ($b_1$) can be associated with Fc-Protein A interaction and the low affinity constant ($b_2$) can be associated with weak nonspecific interactions between Fab fragments on two separate IgG molecules. At low concentrations, the high affinity of IgG for Protein A dominates and Fab fragments are less likely to interact. As a result, IgG binding at low concentrations follows the single-site model well. At higher concentrations, surface crowding due to increased surface density of IgG most likely leads to steric hindrance and nonspecific interactions between Fab fragments. As a result, at higher concentrations, IgG binding follows the two-site Langmuir model better. Previous studies have also reported the surface-crowding phenomenon by IgG at high concentration and have employed the two-site model.

More interesting is the nearly two order of magnitude difference between the two high-affinity constants ($b_1$) for tyrosinase-catalyzed Protein A and that of the control. This indicates that tyrosinase-catalyzed Protein A is more likely to be in orientations on the surface that strongly favor antibody binding. The glutaraldehyde-reacted Protein A is likely attached in a much wider distribution of orientations, many of which are less favorable for IgG binding. FIG. 18 schematically depicts the differences between the two methods of Protein A immobilization, showing how both the capacity and affinity for IgG binding can be altered through orientation control. If the bound IgG is a specific antibody to a particular target protein, the orientation control demonstrated here by the tyrosinase-catalyzed immobilization of Protein A should result in improved sensitivity over glutaraldehyde reaction in a layered expression scanning application for these membranes.

PC-PAA-(tyr)Protein A-IgG Membranes Specifically Capture Target Proteins

Figure 19:
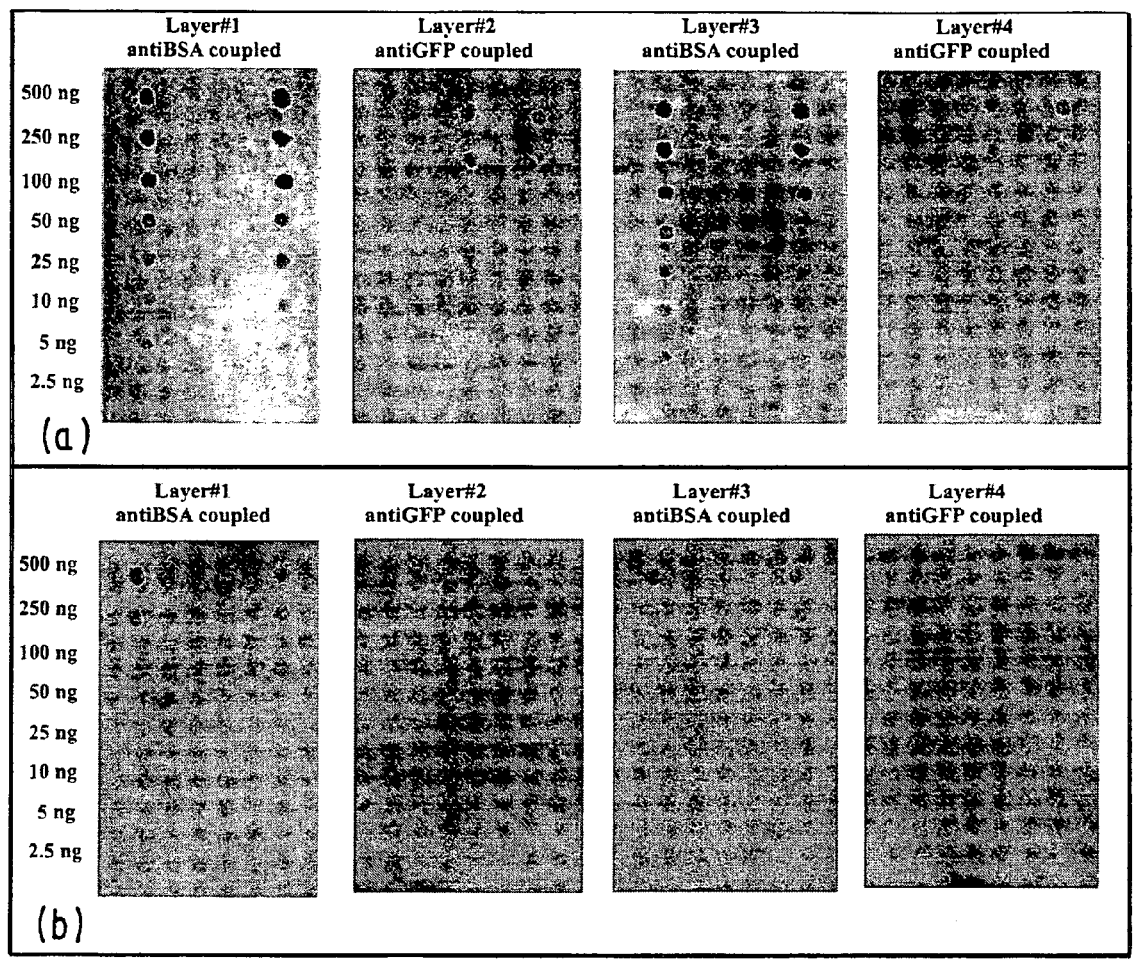
FIG. 19 is a comparison of specific protein capture by antibodies attached to layered membranes: (a) PC-PAA-(tyr) Protein A-IgG, (b) PC-PAA-(g)Protein A-IgG. IgG=antiBSA for Layers #1 and #3. IgG=antiGFP for Layers #2 and #4.
Figure 20:
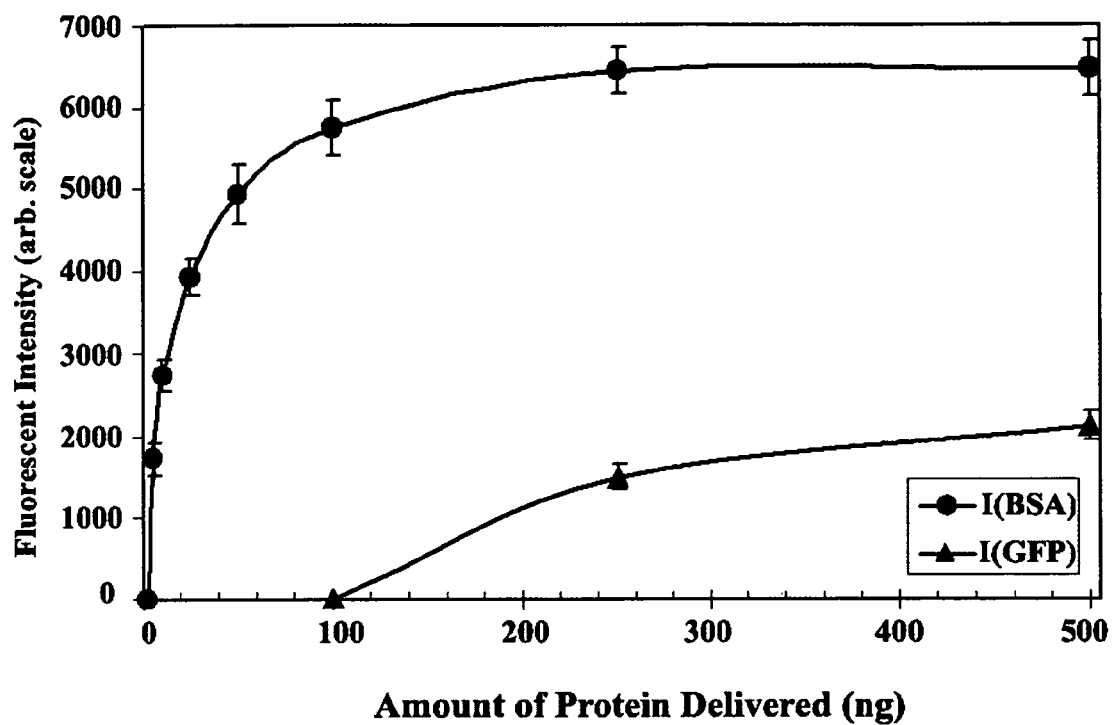
FIG. 20 is a graph showing the quantitative characterization (N=3) of protein capture on (a) PC-PAA-(tyr)Protein A-antiBSA (Layer #1) and (b) PC-PAA-(tyr)Protein A-antiGFP (Layer #2)

Given the results above, it was expected that PC-PAA-(tyr) Protein A-IgG membranes, where FITC-IgG is replaced with either antiBSA or antiGFP, would selectively bind their target protein antigen (BSA or GFP, respectively) to a significantly greater extent than their glutaraldehyde-immobilized Protein A counterparts. Fluorescence scanning of each membrane in the stack showed that the PC-PAA-(tyr)Protein A-IgG membranes indeed had very high specificities for their respective target proteins, as BSA was bound only to membranes with immobilized antiBSA and GFP was bound only to the membranes with immobilized antiGFP (FIG. 19a). In this figure, the first, second and third columns on each membrane represent BSA, GFP and the BSA/GFP mixture, respectively. The membranes can detect protein quantitatively and have a detection limit of 5 ng for BSA and 250 ng for GFP (FIG. 20). The reason for the low detection capability of GFP is due to its weak intrinsic fluorescence (two orders of magnitude less than AF647-BSA). Also shown (FIG. 19b) are the results for a four-layer stack containing control membranes, PC-PAA-(g)Protein A-IgG, which could not detect BSA below 250 ng, and could not detect GFP at all. These results support the hypothesis that antibody orientation is more favorable using tyrosinase-catalyzed immobilization of Protein A.

Time-scale for Protein Binding

Figure 21:
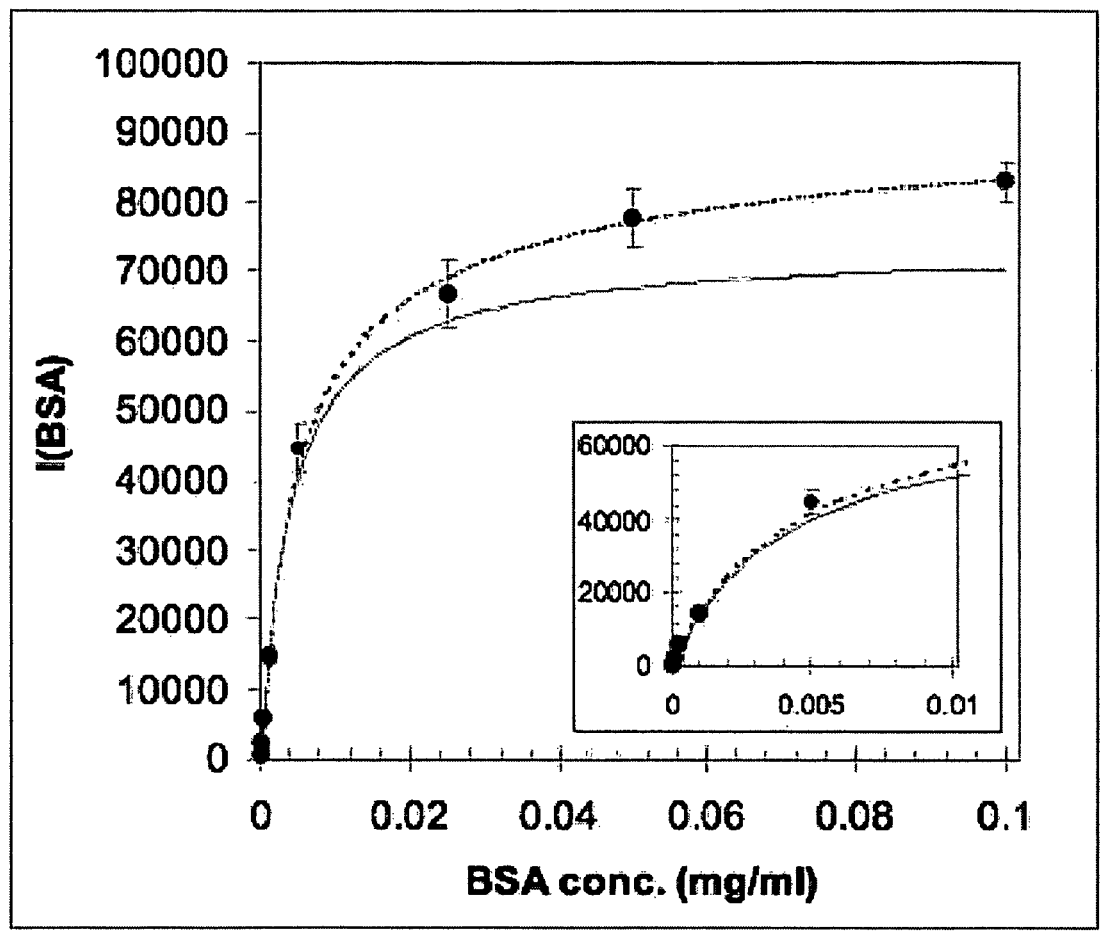
FIG. 21 is a graph showing the BSA binding isotherm on PC-PAA-(tyr)Protein A-antiBSA membranes (N=3). Parameters for single-site (solid line) and two-site (dotted line) Langmuir models are listed in Table 1.

The equilibrium binding isotherm for BSA on PC-PAA-(tyr)Protein A-antiBSA membranes is shown in FIG. 21. The membranes have the potential (at equilibrium) to detect BSA concentrations as low as 5 ng/ml. The data were fit to single-site and two-site Langmuir models given by equations 2 and 3 above. The resulting parameters from regression of the two models are listed in Table 4. Deviations from the single-site model at higher concentrations are likely the result of non-specific protein-protein interactions between BSA molecules. The high binding affinity from the single-site model, b=238 ml/mg, supports the idea that the antiBSA immobilized to the PC-PAA-(tyr)Protein A membrane is oriented favorably for binding to the target protein. In contrast, antiBSA bound to PC-PAA-(g)Protein A controls had a very low binding capacity and could not detect BSA below 25 µg/ml concentration (not shown here).

TABLE 4

Fitting parameters for single-site and two-site Langmuir models for BSA binding to PC-PAA(tyr)-Protein A-antiBSA membranes at 4° C.

| Model | $I_{N1}^{sat}$ | $b_1$ (ml/mg) | $I_{N2}^{sat}$ | $b_2$ (ml/mg) |
|---|---|---|---|---|
| Single-site | 73440 | 238 | — | — |
| Two-site | 73440 | 238 | 19500 | 19 |

Figure 22:
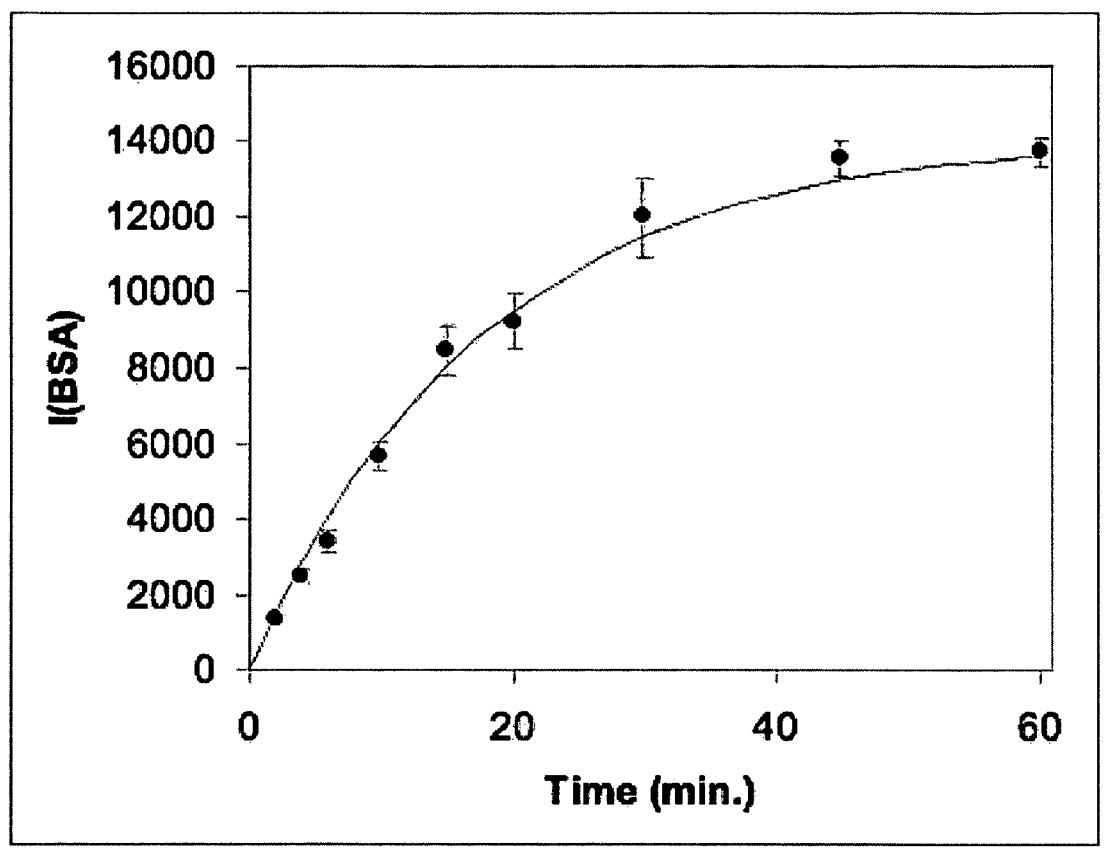
FIG. 22 is a graph showing BSA binding kinetics at C=1 μg/ml (N=3). Line is best fit using equation (3) with $I_N^{sat}$=73, 440 and b=238 ml/mg, fixed from the single-site Langmuir model fit from FIG. 7, and $k_r$=0.045 min$^{-1}$ from regression (R$^2$=0.995)

The single-site Langmuir isotherm given by equation 2 can be derived from the following expression for adsorption kinetics in a Langmuir framework:

$$\frac{dI_N}{dt} = k_r[b(I_N^{sat} - I_N)C - I_N] \quad (4)$$

where $k_r$ is the desorption rate constant, $b=k_f/k_r$, and $k_f$ is the adsorption rate constant. The solution concentration, C, was held constant by insuring a large solution volume relative to membrane area. This differential equation was solved for $I_N$ as a function of time and the fit with $k_r$ as the only adjustable parameter is shown in FIG. 22. The excellent agreement further supports using a Langmuir model at low concentrations to describe protein capture (as a function of both time and concentration).

From FIG. 22, it is clear that the time scale for BSA binding to reach equilibrium on PC-PAA-(tyr)Protein A-antiBSA membranes is on the order of 40 minutes. The spotting experiments (dot blots) were carried out for 10 minutes, during which time the solution is drawn through the stack of membranes by capillarity. Therefore, the exposure (residence) time here for each membrane during protein capture is no longer than 10 minutes, likely much less, with even shorter times for those membranes furthest from the original spot. The result of a shorter exposure time (less binding) is qualitatively apparent when comparing Layer #3 with Layer #1 in FIG. 19a. Clearly, the sensitivity of these affinity membranes for protein detection could be increased by as little as a factor of 2 for the uppermost layer, but by as much as a factor of 10 for a layer deep in a multimembrane stack that may be in contact with protein solution for only 1 minute. Flowrate through a stack of affinity membranes can be easily varied by changing the pore size of the track-etched PC membranes, the pressure difference across them, or a combination of both. A number of pore sizes and pore densities are available. Therefore, it should be possible to optimize the residence time for each layer to obtain the highest possible sensitivity for protein capture.

PC-PAA-(tyr)Protein A-IgG Membranes can Reproduce Morphological Information

Figure 23:
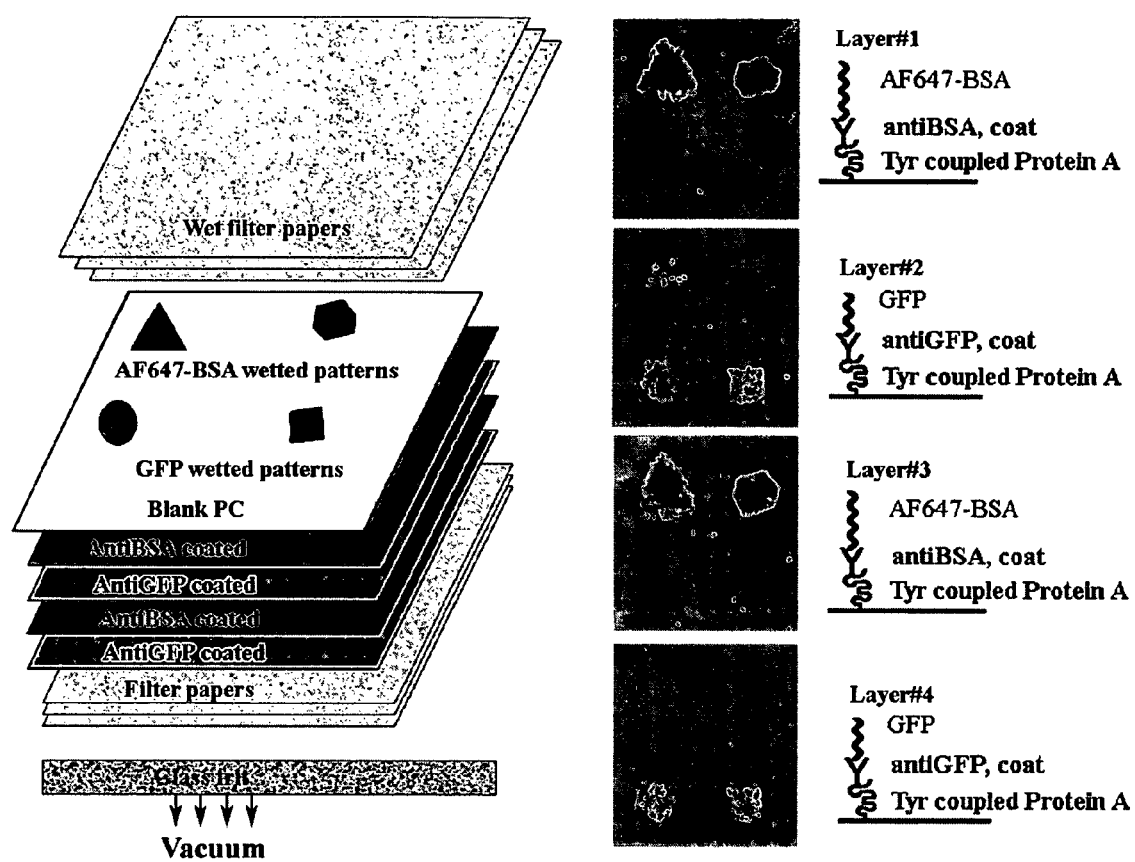
FIG. 23 illustrates that PC-PAA-(tyr)Protein A-IgG membranes can capture morphological features from four shapes pre-wetted with target proteins.

To demonstrate the ability to capture sample morphology (as would be relevant in tissue sections), pieces of filter paper were cut into different patterns (circle, triangle, square and hexagon) and each pattern was soaked in either 50 µg/ml of AF647-BSA (triangle, hexagon) or 1 mg/ml of GFP (circle, square). The protein containing patterns were placed on the layered membrane stacks and covered with several pieces of 1× PBS wetted filter paper. The stacks were then placed on a glass frit and a weak vacuum was applied at the bottom of the frit. After 15 minutes, the membranes were washed twice with 1× TBST for 10 minutes to remove nonspecifically bound proteins from the membrane surfaces and placed on glass slides for scanning. Fluorescence images showed that each membrane specifically captured only its target protein and also retained the morphological information from the pattern (FIG. 23).

CONCLUSIONS

Affinity membranes based on the immobilization of Protein A to amine groups on a polyallylamine surface were developed for potential use in layered expression scanning, a high-throughput multimembrane blotting application. The Protein A was immobilized through the tyrosinase-catalyzed reaction of tyrosine residues to the surface. Track-etched polycarbonate served as the base membrane, which was surface modified for the polyallylamine layer using a compatibilizing tie layer. The immobilization of Protein A by this enzymatic method resulted in a surface with both enhanced capacity (by a factor of 30) and affinity (by a factor of 100) for binding antibody (IgG) relative to immobilization through glutaraldehyde chemistry.

Membranes capable of specifically capturing BSA and GFP were fabricated by coupling IgG (either antiBSA or antiGFP) to the immobilized Protein A. Antibodies coupled to tyrosinase-immobilized Protein A captured their specific target proteins (either BSA or GFP) with very high specificity in dot blot experiments and had a detection limit of 5 ng/ml for BSA and 250 ng/ml for GFP. The lower detection capability for GFP is due to its weaker intrinsic fluorescent intensity. In contrast, antiBSA coupled to glutaraldehyde-immobilized Protein A had a very low binding capacity and could not detect BSA below 25 µg/ml and could not detect GFP at all. The results indicate that tyrosinase-immobilized Protein A can strongly bind significant amounts of IgG (suggestive of a single orientation or a very narrow distribution of orientations), which, in turn, leads to properly oriented IgG, with very high specificity towards target antigens. Equilibrium BSA binding to antiBSA followed a single-site Langmuir model at concentrations below 10 µg/ml, and the binding data as a function of time at a fixed concentration were well described by Langmuir kinetics. The time scale for protein capture during a blotting transfer in a multimembrane stack must be further optimized against that for protein binding kinetics for maximum sensitivity. The membranes can retain morphological information and have the potential to image the localization of protein expression in tissue sections.

Additional work is necessary to demonstrate that the affinity membranes developed here can achieve the high selectivity required for high throughput LES. Although the use of tyrosinase for the site-directed immobilization of Protein A results in orientations that are more favorable for subsequent antibody (IgG) binding than random glutaraldehyde chemistry, it is not clear if there is one or more preferred tyrosine residues for attachment. Mapping the tyrosines that are accessible to tyrosinase or using amino acid substitutions could lead to further optimization of Protein A immobilization by this approach. In addition, investigating other sources for the Protein A, the substitution of Protein G, or the use of sub-units of these Fc-binding proteins could also lead to improvements in antibody orientation. Further characterization of the amine-functional layer, including its stability, is also important.

To further demonstrate the protein capture capabilities of the membranes, a more quantitative analysis of the actual amount of captured protein should be undertaken. Also, since the ability to capture a particular protein should be independent of the affinity membrane's location in the stack, further experiments should focus on this hypothesis. The important finding here that the kinetics of protein capture may limit sensitivity suggests further experiments to determine if pore size and pressure drop can be varied to control residence time in a membrane stack. Lastly, actual protein samples, such as sera, should be tested with these affinity membranes using a secondary antibody detection system.

Many modifications and variations of the present disclosure are possible in light of the above teachings. It is, therefore, to be understood within the scope of the appended claims the invention may be protected otherwise than as specifically described.

What we claim is:

1. A membrane-containing composition that directs the orientation of an immobilized peptide or protein on a hydrophobic membrane, said composition comprising:

a) at least one said hydrophobic membrane, said at least one said hydrophobic membrane being selected from the group consisting of a thin porous substrate with straight pores, a polycarbonate membrane, and a track etched membrane;
b) at least one tie layer layered on said hydrophobic membrane, said tie layer being selected from the group consisting of polyvinyl acetate and polyvinyl butyral;
c) an amine functional layer layered on top of said at least one tie layer; said amine-functional layer being nickel-coordinated chitosan;
d) a plurality of peptides or proteins comprising a histidine tag, wherein said histidine tag is attached to said nickel of said nickel-coordinated chitosan, and wherein said immobilized peptides or proteins are aligned on said amine functional layer, and wherein said peptides or proteins are capable of binding to antibodies or target biomolecules.

2. A composition comprising a plurality of said membrane-containing compositions of claim 1, wherein said membrane-containing compositions form a stack, and wherein each membrane-containing composition is positioned on top of and in contact with another membrane-containing composition.

3. The composition according to claim 1, wherein said tie layer is soluble in a solvent having a polarity ranging between that of a solvent in which the nickel-coordinated chitosan is soluble to that of a solvent in which the polycarbonate layer is soluble.

* * * * *